(12) United States Patent
Chen

(10) Patent No.: US 7,919,585 B2
(45) Date of Patent: Apr. 5, 2011

(54) B7-H5, A COSTIMULATORY POLYPEPTIDE

(75) Inventor: Lieping Chen, Sparks Glencoe, MD (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 466 days.

(21) Appl. No.: 11/571,195

(22) PCT Filed: Jun. 24, 2005

(86) PCT No.: PCT/US2005/022321
§ 371 (c)(1),
(2), (4) Date: Jan. 24, 2008

(87) PCT Pub. No.: WO2006/012232
PCT Pub. Date: Feb. 2, 2006

(65) Prior Publication Data
US 2008/0248007 A1    Oct. 9, 2008

Related U.S. Application Data

(60) Provisional application No. 60/582,491, filed on Jun. 24, 2004.

(51) Int. Cl.
*C07K 14/00* (2006.01)
(52) U.S. Cl. .................................................. 530/350
(58) Field of Classification Search .................. None
See application file for complete search history.

(56) References Cited

U.S. PATENT DOCUMENTS

| 6,924,355 | B2 * | 8/2005 | Baker et al. ............. 530/350 |
| 7,655,778 | B2 | 2/2010 | Yang |
| 2003/0073129 | A1 * | 4/2003 | Baker et al. ............. 435/7.1 |
| 2007/0048301 | A1 * | 3/2007 | Bodary-Winter et al. . 424/143.1 |

FOREIGN PATENT DOCUMENTS

| CN | 1351081 A | 10/2000 |
| WO | WO 00/78961 A1 | 12/2000 |
| WO | WO01/04297 | 1/2001 |
| WO | WO 01/93983 A1 | 12/2001 |
| WO | WO 02/00690 A2 | 1/2002 |
| WO | WO 02/08284 A2 | 1/2002 |
| WO | WO 02/08288 A2 | 1/2002 |
| WO | WO 02/057303 A2 | 7/2002 |
| WO | WO 2004/047728 A2 | 6/2004 |
| WO | WO 2005/019258 A | 3/2005 |
| WO | WO 2006/012232 A1 | 2/2006 |
| WO | WO 2006/098887 A2 | 9/2006 |
| WO | WO 2007/100211 A1 | 9/2007 |
| WO | WO 2010/027827 A2 | 3/2010 |

OTHER PUBLICATIONS

Sequence alignment, 2010, 4 pages.*
Sequence alignment, 2010, 1 page.*
Strausberg et al., Generation and initial analysis of more than 15,000 full length human and mouse cDNA sequences: Mammalian Gene Collection (MGC) Program Team, PNAS, Dec. 24, 2002, 99(26):16899-16903.
Database EMBL, Sep. 29, 2000, "Homosapiens mRNA for FLJ00041 Protein, Partial CDS", EMBL: AK024449.
Database EMBL, Sep. 8, 2001, "Mus Musculus 0 Day Neonate Skin cDNA, Riken Full-Length Enriched Library, Clone: 4632428N05 Product: Hypothetical Immunoglobulin and Major Histocompatibility Complex Domain/Immunoglobulin Subtype containing Protein, Full Insert Sequence", XP002444245, EMBL: AK014600.

* cited by examiner

*Primary Examiner* — Ilia Ouspenski
(74) *Attorney, Agent, or Firm* — Fish & Richardson P.C.

(57) ABSTRACT

B7-HS costimulatory polypeptides, nucleic acids encoding such polypeptides, and methods for using the polypeptides and nucleic acids to enhance a T cell response are provided herein.

25 Claims, 13 Drawing Sheets

Fig. 1

CCGGCCGCGTCCCGCCCGCTCCCCGGCACCAGAAGTTCCTCTGCGCGTCCGACGGCGAC<u>ATG</u>GGCGTCCCCACGGCCCTGGA
GGCCGGCAGCTGGCGCTGGGGATCCCTGCTCTTCGCTCTCTTCCTGGCTGCGTCCCTAGGTCCGGTGGCAGCCTTCAAGGTC
GCCACGCCGTATTCCCTGTATGTCTGTCCCGAGGGGCAGAACGTCACCCTCACCTGCAGGCTCTTGGGCCCTGTGGACAAAG
GGCACGATGTGACCTTCTACAAGACGTGGTACCGCAGCTCGAGGGGCGAGGTGCAGACCTGCTCAGAGCGCCGGCCCATCCG
CAACCTCACGTTCCAGGACCTTCACCTGCACCATGGAGGCCACCAGGCTGCCAACACCAGCCACGACCTGGCTCAGCGCCAC
GGGCTGGAGTCGGCCTCCGACCACCATGGCAACTTCTCCATCACCATGCGCAACCTGACCCTGCTGGATAGCGGCCTCTACT
GCTGCCTGGTGGTGGAGATCAGGCACCACCACTCGGAGCACAGGGTCCATGGTGCCATGGAGCTGCAGGTGCAGACAGGCAA
AGATGCACCATCCAACTGTGTGGTGTACCCATCCTCCTCCCAGGAGAGTGAAAACATCACGGCTGCAGCCCTGGCTACGGGT
GCCTGCATCGTAGGAATCCTCTGCCTCCCCCTCATCCTGCTCCTGGTCTACAAGCAAAGGCAGGCAGCCTCCAACCGCCGTG
CCCAGGAGCTGGTGCGGATGGACAGCAACATTCAAGGGATTGAAAACCCCGGCTTTGAAGCCTCACCACCTGCCCAGGGGAT
ACCCGAGGCCAAAGTCAGGCACCCCCTGTCCTATGTGGCCCAGCGGCAGCCTTCTGAGTCTGGGCGGCATCTGCTTTCGGAG
CCCAGCACCCCCCTGTCTCCTCCAGGCCCCGGAGACGTCTTCTTCCCATCCCTGGACCCTGTCCCTGACTCTCCAAACTTTG
AGGTCATC<u>TAG</u>CCCAGCTGGGGGACAGTGGGCTGTTGTGGCTGGGTCTGGGGCAGGTGCATTTGAGCCAGGGCTGGCTCTGT
GAGTGGCCTCCTTGGCCTCGGCCCTGGTTCCCTCCCTCCTGCTCTGGGCTCAGATACTGTGACATCCCAGAAGCCCAGCCCC
TCAACCCCTCTGGATGCTACATGGGGATGCTGGACGGCTCAGCCCCTGTTCCAAGGATTTTGGGGTGCTGAGATTCTCCCCT
AGAGACCTGAAATTCACCAGCTACAGATGCCAAATGACTTACATCTTAAGAAGTCTCAGAACGTCCAGCCCTTCAGCAGCTC
TCGTTCTGAGACATGAGCCTTGGGATGTGGCAGCATCAGTGGGACAAGATGGACACTGGGCCACCCTCCCAGGCACCAGACA
CAGGGCACGGTGGAGAGACTTCTCCCCCGTGGCCGCCTTGGCTCCCCCGTTTTGCCCGAGGCTGCTCTTCTGTCAGACTTCC
TCTTTGTACCACAGTGGCTCTGGGGCCAGGCCTGCCTGCCCACTGGCCATCGCCACCTTACCCAGCTGCCTCCTACCAGCAG
TTTCTCTGAAGATCTGTCAACAGGTTAAGTCAATCTGGGGCTTCCACTGCCTGCATTCCAGTCCCCAGAGCTTGGTGGTCCC
GAAACGGGAAGTACATATTGGGGCATGGTGGCCTCCGTGAGCAAATGGTGTCTTGGGCAATCTGAGGCCAGGACAGATGTTG
CCCCACCCACTGGAGATGGTGCTGAGGGAGGTGGGTGGGGCCTTCTGGGAAGGTGAGTGGAGAGGGGCACCTGCCCCCCGCC
CTCCCCATCCCCTACTCCCACTGCTCAGCGCGGGCCATTGCAAGGGTGCCACACAATGTCTTGTCCACCCTGGGACACTTCT
GAGTATGAAGCGGGATGCTATTAAAAACTACATGGGGAAACAGGTGCAAACCCTGGAGATGGATTGTAAGAGCCAGTTTAAA
TCTGCACTCTGCTGCTCCTCCCCCACCCCCACCTTCCACTCCATACAATCTGGGCCTGGTGGAGTCTTCGCTTCAGAGCCAT
TCGGCCAGGTGCGGGTGATGTTCCCATCTCCTGCTTGTGGGCATGCCCTGGCTTTGTTTTTATACACATAGGCAAGGTGAGT
CCTCTGTGGAATTGTGATTGAAGGATTTTAAAGCAGGGGAGGAGAAGTAGGGGGCATCTCTGTACACTCTGGGGGTAAAACAG
GGAAGGCAGTGCCTGAGCATGGGGACAGGTGAGGTGGGGCTGGGCAGACCCCCTGTAGCGTTTAGCAGGATGGGGGCCCCAG
GTACTGTGGAGAGCATAGTCCAGCCTGGGCATTTGTCTCCTAGCAGCCTACACTGGCTCTGCTGAGCTGGGCCTGGGTGCTG
AAAGCCAGGATTTGGGGCTAGGCGGGAAGATGTTCGCCCAATTGCTTGGGGGGTTGGGGGGATGGAAAAGGGGAGCACCTCT
AGGCTGCCTGGCAGCAGTGAGCCCTGGGCCTGTGGCTACAGCCAGGGAACCCCACCTGGACACATGGCCCTGCTTCTAAGCC
CCCCAGTTAGGCCCAAAGGAATGGTCCACTGAGGGCCTCCTGCTCTGCCTGGGCTGGGCCAGGGGCTTTGAGGAGAGGGTAA
ACATAGGCCCGGAGATGGGGCTGACACCTCGAGTGGCCAGAATATGCCCAAACCCCGGCTTCTCCCTTGTCCCTAGGCAGAG
GGGGGTCCCTTCTTTTGTTCCCTCTGGTCACCACAATGCTTGATGCCAGCTGCCATAGGAAGAGGGTGCTGGCTGGCCATGG
TGGCACACACCTGTCCTCCCAGCACTTTGCAGGGCTGAGGTGGAAGGACCGCTTAAGCCCAGGTGTTCAAGGCTGCTGTGAG
CTGTGTTCGAGCCACTACACTCCAGCCTGGGGACGGAGCAAAACTTTGCCTCAAAACAAATTTTAAAAAGAAAGAAAGAAGG
AAAGAGGGTATGTTTTTCACAATTCATGGGGCCTGCATGGCAGGAGTGGGGACAGGACACCTGCTGTTCCTGGAGTCGAAG
GACAAGCCCACAGCCCAGATTCCGGTTCTCCCAACTCAGGAAGAGCATGCCCTGCCCTCTGGGGAGGCTGGCCTGGCCCCAG
CCCTCAGCTGCTGACCTTGAGGCAGAGACAACTTCTAAGAATTTGGCTGCCAGACCCCAGGCCTGGCTGCTGCTGTGTGGAG
AGGGAGGCGGCCCGCGGCAGAACAGCCACCGCACTTCCTCCTCAGCTTCCTCTGGTGCGGCCCTGCCCTCTCTTCTCTGGAC
CCTTTTACAACTGAACGCATCTGGGCTTCGTGGTTTCAGCGAAATTTACTCTGAGCTCCCAGTTCCATCTTCAT
CCATGGCCACAGGCCCTGCCTACAACGCACTAGGGACGTCCCTCCCTGCTGCTGCTGGGGAGGGGCAGGCTGCTGGAGCCGC
CCTCTGAGTTGCCCGGGATGGTAGTGCCTCTGATGCCAGCCCTGGTGGCTGTGGGCTGGGGTGCATGGGAGAGCTGGGTGCG
AGAACATGGCGCCTCCAGGGGCGGGAGGAGCACTAGGGGCTGGGGCAGGAGGCTCCTGGAGCGCTGGATTCGTGGCACAGT
CTGAGGCCCTGAGAGGGAAATCCATGCTTTTAAGAACTAATTCATTGTTAGGAGATCAATCAGGAATTAGGGGCCATCTTAC
CTATCTCCTGACATTCACAGTTTAATAGAGACTTCCTGCCTTTATTCCCTCCCAGGGAGAGGCTGAAGGAATGGAATTGAAA
GCACCATTTGGAGGGTTTTGCTGACACAGCGGGGACCGCTCAGCACTCCCTAAAAACACACCATGGAGGCCACTGGTGACTG
CTGGTGGGCAGGCTGGCCCTGCCTGGGGGAGTCCGTGGCGATGGGCGCTGGGGTGGAGGTGCAGGAGCCCCAGGACCTGCTT
TTCAAAAGACTTCTGCCTGACCAGAGCTCCCACTACATGCAGTGGCCCAGGGCAGAGGGCTGATACATGGCCTTTTTCAGG
GGGTGCTCCTCGCGGGGTGGACTTGGGAGTGTGCAGTGGGACAGGGGGCTGCAGGGGTCCTGCCACCACCGAGCACCAACTT
GGCCCCTGGGGTCCTGCCCCATGAATGAGGCCTTCCCCAGGGCTGGCCTGACTGTGCTGGGGGCTGGGTTAACGTTTTCTCA
GGGAACCACAATGCACGAAAGAGGAACTGGGGTTGCTAACCAGGATGCTGGGAACAAAGGCCTCTTGAAGCCCAGCCACAGC
CCAGCTGAGCATGAGGCCCAGCCCATAGACGGCACAGGCCACCTGGCCCATTCCCTGGGCATTCCCTGCTTTGCATTGCTGC
TTCTCTTCACCCCATGGAGGCTATGTCACCCTAACTATCCTGGAATGTGTTGAGAGGGATTCTGAATGATCAATATAGCTTG
GTGAGACAGTGCCGAGATAGATAGCCATGTCTGCCTTGGGCACGGGAGAGGGAAGTGGCAGCATGCATGCTGTTTCTTGGCC
TTTTCTGTTAGAATACTTGGTGCTTTCCAACACACTTTCACATGTGTTGTAACTTGTTTGATCCACCCCCTTCCCTGAAAAT
CCTGGGAGGTTTTATTGCTGCCATTTAACACAGAGGGCAATAGAGGTTCTGAAAGGTCTGTGTCTTGTCAAAACAAGTAAAC
GGTGGAACTACGACT (SEQ ID NO:5)

Fig. 2

```
GAGCATTCACTCTAGCGAGCGAGCGGCGTGTACAGCCGGCTCCCTGGGCTCCTGGAGTCCCGCTTGCTCCAAGCGCACTCCAG
CAGTCTCTTTCTGCTCTTGCCCGGCTCGACGGCGACATGGGTGTCCCCGCGGTCCCAGAGGCCAGCAGCCCGCGCTGGGGAAC
CCTGCTCCTTGCTATTTTCCTGGCTGCATCCAGAGGTCTGGTAGCAGCCTTCAAGGTCACCACTCCATATTCTCTCTATGTGT
GTCCCGAGGGACAGAATGCCACCCTCACCTGCAGGATTCTGGGCCCCGTGTCCAAAGGGCACGATGTGACCATCTACAAGACG
TGGTACCTCAGCTCACGAGGCGAGGTCCAGATGTGCAAAGAACACCGGCCCATACGCAACTTCACATTGCAGCACCTTCAGCA
CCACGGAAGCCACCTGAAAGCCAACGCCAGCCATGACCAGCCCCAGAAGCATGGGCTAGAGCTAGCTTCTGACCACCACGGTA
ACTTCTCTATCACCCTGCGCAATGTGACCCCAAGGGACAGCGGCCTCTACTGCTGTCTAGTGATAGAATTAAAAAACCACCAC
CCAGAACAACGGTTCTACGGGTCCATGGAGCTACAGGTACAGGCAGGCAAAGGCTCGGGGTCCACATGCATGGCGTCTAATGA
GCAGGACAGTGACAGCATCACGGCTGCGGCCCTGGCCACCGGCGCCTGCATCGTGGGAATCCTCTGCCTCCCCCTTATCCTGC
TGCTGGTCTATAAGCAGAGACAGGTGGCCTCTCACCGCCGTGCCCAGGAGTTGGTGAGGATGGACAGCAGCAACACCCAAGGA
ATCGAAAACCCAGGCTTCGAGACCACTCCACCCTTCCAGGGGATGCCTGAGGCCAAGACCAGGCCGCCACTGTCCTATGTGGC
CCAGCGGCAACCTTCGGAGTCAGGACGGTACCTGCTCTCTGACCCCAGCACACCTCTGTCGCCTCCAGGCCCTGGGGACGTCT
TTTTCCCATCCCTAGATCCAGTCCCTGACTCCCCTAACTCTGAAGCCATCTAAACCAGCTGGGGAACCATGAACCATGGTACC
TGGGTCAGGGATATGTGCACTTGATCTATGGCTGGCCCTTGGACAGTCTTTTAGGCACTGACTCCAGCTTCCTTGCTCCTGCT
CTGAGCCTAGACTCTGCTTTTACAAGATGCACAGACCCTCCCCTATCTCTTTCAGACGCTACTTGGGGGGCAGGGAGAAGATG
TTGGATTGCTCATTGCTGTTCTCAAGATCTTGGGATGCTGAGTTCTCCCTAGAGACTTGACTTCGACAGCCACAGATGTCAGA
TGACCTGCATCCTATGAACGTCCGGCTTGGCAAGAGCCTTTCTTCATGGAAACCAGTAGCCCGGAGGGGATGAGGTAGGCACC
TTGCCACCCTCCCGGGAGAGAGACACAAGATGTGAGAGACTCCTGCTCACTGTGGGGGTGTGGCTGGCCTGCTTGTTTGCCTG
AGGATGCTCCTCTGTTGGACTGACTCTATCCCCCTGGATTCTGGAGCTTGGCTGGCCTATGTCCCACCAGAGGAGCATCTCAG
CAGCCTTCCACCAGCAACCTGAGGGCCTGCCAGCTTCGTGGCTCTGGGCTCTCATTACCTGTATGGCCGTCCACAGAGCTCAG
TGGCCAGAGGCTTTGAAACAGGAAGTACATGTCAGGTTCAGGAACCACTGTGAGCTCATTAGTGTCTTGAGCAATGTGAGGCC
TGGACCAGTGGACACGGAGGGAGGGTGGCGAGAGGATGATGGGGATGATGAGGGGAACACGCTCCCTTCCTGTCCTTGTCATC
CACCACTACCACTATTCAGTGTGGAGCAGTGGCAAAGGTGACCGACCTCCACAATGTCCTAGTGATGCTGGACCATTTCTAAG
TGTGAAAGAGATGCTATTAAAAACAGTATGTGGCAATGGCTGCCAACAGCTGAGTGGACTGGAGGCACTGGCTTTAAGGCCCT
GGAGGTGCAGGGCCCGGTATGGGGATAGGGATGGGAGTTTCAGTGAGGGCCTAGGGATCACTCCGCTTCTGACCACTCTTCTT
CTGAGCCTCACCTCAGGGTGACCTTCAGGCACACAGAAGAGCTTGCCCCTGGTCCGATACTACTCTTGGCTCTCATCTCCAGG
GTTTGGCATGACCTGGGCACACAGGGGGAGTCTTCAGAAAGGATTTTAAAGCATGAAAAGAAAGGGTAGTTCTTGTGAGGTAG
GGATGGGCAGCTGATGTTTGAGAGTGAGGAGGGATACGGCTGGGCAGATCACTCTCCAGTCTCTAGAGGGAAAGTAGCTCTAA
GTCTGGGAGAGCAGCAGCCCAGTGGTACCATATGTCTTCTTGCAGCTTCCACTGGCTGGGCTGAACTGGGCATGGGTAGGAAA
GCTCCTGTTCTGGGCCTGCAGCCAGGGAGAACCCCATTCATTCCCTGAGGACAGATGGGTGGGGAGAGAAGAGAGAGTTTCAG
GCCGGGAAGCAGCAATAAGCTATCTGCTGGGGACCCAGACAAGTTGTCTGATGAGGTCCAAGATGTGGGATGCCAGTTATACC
TGGGGCTTGGGGATCCTTAGAGGCTTTGTATCATCATATAGGAGTGTCGGGGTGGCCAGGGCATCAAAGCCATGACCCCTGT
TTTATCCTCAGGGTCCACTCTTCTGCACCATCCATTGCTCTAGATCTATGCAGTTACTATAGACAGAATGTGTTGTTCTGTTT
GGCTTTGGGGATAATGGCCTGGCGAACTGCCAGCTGTTCAGTGGCAGGGCTGTGAGGCCAGTCAAAGACTAGAACCCACAGAC
CAGCTGAACGATGAGTATAGCCTGTCCCCTGGGGGAGCCTGACCTGTCTCCAGCCCTAAGCTTCAGACCTCACCACTCAGATG
ACTTCTAAGAATTTGCCTGTGGGGACCCCTGCATGGCTGCAGCTCCGTGGAAAGGAGAGGAGGCCCCAGCAGAAGAACCACT
CGCTTCCTGCCCAGCTTCCTCCTGTAGGGCTCTAAGTCTCTTCTTCTTGGGACCCTGCAAGCAAAGGCATGTCAGCTTGGTGG
TTTCCTGTTTTGGGTGAAGTTTTGTGTGGTCCGGGTTCTGTCTACATCCATGAACTTGGGGTGCTACCACCTTGCTGCTGCTG
TAGAGACAGCTGCAGGATCTTAGGGTGGAAAATGGAGGTGCCCTGAGGTGCTAGCCCTTGGGGCAAAAGATGGGGTGGCAATG
AGACACAGTGGGGAACTGAGTTCCCCAAGAGGAGGGAGGAGCCCTGTAGCCTCAAGGGCCATATTGGGTTCCTGGTACCAGCA
AAAGCCTAGAGAGCGAAGTCTGTATTTTGAGGAGGTAATTGATCCTTACGGAATCCATCAGAAATTTGGAGCGGGTGCTTTAT
CTATCTCTGGAGGGTCTCTACCTATCTCCGATGAAGCTCTCCCTGGGCCTGGGATGGAGAAACCAGGAGGAAAGGTGTCTGA
TAAAGCAGGGGCTTCTTGACAAGCCAAAGGGCCACTGGTAGCTGTTGTGGACCGAGCTGACCCTGCTGAAGTATTGTAGTGTG
CCTTGGACCAACTTCTCAAAAGAGCAACCCCGGGCTACCCTACTTCTGCCAGGAAGAGGCGGAGAAGGGGCTGAGAGGCCTG
GAAGGGGCTAGCTCCTTCTTTGAGAACTGCTCCCCGGAGGACTTGGAGGAGGCGGCTAGGCTACGGGCTGCTGAGGGCCCTTT
GTCTTTCCTAACCTGGGCACTGTTAGGATGCTCCCTCCTGGAAAAGGCTTTCCTGGGTGTGAGCTAGAGCAGTGTCCATGCCA
GCGCTGAACCTGCCATGGTGGGAGCTGAACTAAAAATTTCTCAGGGAACTAAAATAGGCAAAAGAGGAACTGGGGAGGAGGG
TGCCAGGCAGGATGGGGGAAGGGAGGGCAGTGCAAAAGTCTCTTGAAACACAGACAGCCCAGCTGAGTGCCAGTCCCAGATC
ACAGAGAATACGGCTCATCTGGCTCATGTTCTGCATGCTTGCTGCTTTACCCTGGCACTTTCCTTCTCCACCATGAGTGCGAG
TCCTGGGAGTCCTGGGAGGGTGAGGATTAATGCCAGCCTGGGGAGCAGATAGCTGACAGAGTCCTTGGGTAACTGGCTTGAAC
CAGGACCTCAGGATTCCACTCTGGGGATCTAGCTTTGTCTGGCCAGTGAAGATCTCTATAATGGCATTATTGCCAGGGGATA
AACATTTCACTGGGTTCTGATCTGTTGGGTGTGGCTTCCTGGAAAATATGGTGAGAGGAATTCTGCTAAGGATACAGTTGATA
AGAAAGTTCTGAGATTGATTAGTAATGCCTGCCTTGGACTCAGGAAGGGAAGTGGCAGTATGAATGCCATGTCTTAATCATTT
TGGTTAAAATATGCTTCCCAAAAGATTTCCACGTGTGTTCTTGTTTATTTGACATCTGTCTCCATATCAGTCTTGAAAGCCTT
TCTGTGTGTATATATATGATGTTTGCGTGTATATATGTTTTTGTGTGTGCATATGGAAGTCAGAAATCACTGGGTGTCTTCCT
CCATTCCTTTGCAATGTATGTTTTTTTTTTTTTTACGATTTATTTACTATATGAATGTTTTGCCTGAATACATGCATAGGTGT
CACGTACATGCCTGCTGGAACGCTTGGAACTGGAGTTACAGGTGGCTATGAGCTACAGTGTGAGCACTGGGAATCAAACCTGG
GTCTTCTGCAAGAGCAACAAATTAAAAGTCAGCTCTTAACTACTTGAGCTATTTTTCCAACTCC(SEQ ID NO:6)
```

Fig. 3

MGVPTALEAGSWRWGSLLFALFLAASLGPVAAFKVATPYSLYVC
PEGQNVTLTCRLLGPVDKGHDVTFYKTWYRSSRGEVQTCSERRP
IRNLTFQDLHLHHGGHQAANTSHDLAQRHGLESASDHHGNFSIT
MRNLTLLDSGLYCCLVVEIRHHHSEHRVHGAMELQVQTGKDAPS
NCVVYPSSSQESENITAAALATGACIVGILCLPLILLLVYKQRQ
AASNRRAQELVRMDSNIQGIENPGFEASPPAQGIPEAKVRHPLS
YVAQRQPSESGRHLLSEPSTPLSPPGPGDVFFPSLDPVPDSPNF
EVI (SEQ ID NO:1)

Fig. 4

MGVPAVPEASSPRWGTLLLAIFLAASRGLVAAFKVTTPYSL
YVCPEG<u>QNATLTCRILGPVSKGHDVTIYKTWYLSSRGEVQM
CKEHRPIRNFTLQHLQHHGSHLKANASHDQPQKHGLELASD
HHGNFSITLRNVTPRDSGLYCCLVIELKNHHPEQRFYGSME
LQVQAGKGSGSTC</u>MASNEQDSDS**ITAAALATGACIVGILCL
PLILLLV**YKQRQVASHRRAQELVRMDSSNTQGIENPGFETT
PPFQGMPEAKTRPPLS[Y]VAQRQPSESGR[Y]LLSDPSTPLSPP
GPGDVFFPSLDPVPDSPNSEAI  (SEQ ID NO:3)

Signal sequence   Ig domain   Linker   Transmenbrane region   Low complexity/structured motif

Fig. 6

```
              A'                        B                        C
                              #hph   C                  ##            h   W
hCD80    IH TKE......VKEV ATLS CGH...NVSVE  AQ RIY QK............
hCD86    LK QAY......FNET ADLP CQF..ANSQNQ  SE VVF QD............
hB7-H1   DL VVE......YGSN MTIE CKF..PVEKQL  AA IVY EM............
mB7-H1   DL VVE......YGSN VTME CRF..PVEREL  LA VVY EK............
hB7-H2   KE RAM......VGSD VELS CAC..PEGSRF  ND YVY QT............
hB7-H3   DP VAL......VGTD ATLC CSP..SPEPGP  AQ NLI QL............
hB7-DC   EL IIE......HGSN VTLE CNF..DTGSHV  GA TAS QK............
mB7-DC   EV TVD......VGSS VSLE CDF..DRRECT  EG RAS QK............
hB7-H4   IT TTVAS..AGNIGED GILS CTF....EPDI SD VIQ LK............
mB7-H4   IT TTFTS..AGNIGED GTLS CTF....EPDI NG VIQ LK............
hB7-H5   FK ATPYSLYVCPEGQN VTLT CRLLGPVDKGH  TF KTW RSSRGE VQTCSE
mB7-H5   FK TTPYSLYVCPEGQN ATLT CRILGPVSKGH  TI KTW LSSRGE VQMCKE
              40              50              60              70

C'              C"                    #   D#           E         #
                         *#### *#             ##R#   h####        h#h#p
hCD80    ..EK..K VLT ..MSG MNI....WPE KNRTI DITN....NSIVILA R
hCD86    ..QEN.L LNE ..YLG EKF.DSVHSK MGRTS FDSDS....TLRLHN Q
hB7-H1   ..EDK.N IQF ..H.G EDL.KVQHSS RQRARL LKDQLSLG ALQIT D K
mB7-H1   ..EDE.Q IQF ..A.G EDL.KPQHSN RGRASL PKDQLLKG ALQIT D K
hB7-H2   ..SES.K VVT ..HIP NSSLENVDSR RNRALH SPAGLMRG SLRLF N T
hB7-H3   ..TDT.Q VHS ..AEG DQG.....SA ANRTAL FPDLLAQG SLRLQ R R
hB7-DC   ........ END ..SPH ERA....TL EEQLPLGK...... SFHIP Q
mB7-DC   ........ END ..SLQ ERA....TL EEQLPLGK...... LFHIPS Q
hB7-H4   ..EGVLG VHE ..KEG DEL.SEQDEM RGRTAV FADQVIVG SLRLKN Q
mB7-H4   ..EGIKG VHE ..KEG DDL.SQQHEM RGRTAV FADQVVVG SLRLKN Q
hB7-H5   RRPIRNL FQD HLHHG HQAA.NTSHD AQRHGL ESASDHHG SITMRN T
mB7-H5   HRPIRNF LQH .HHG HLKA.NASHD PQKHGL ELASDHHG SITLRN T
              80              90            100           110           120

F
              D G Y  C*    *    *****       G    h
hCD80    PS DEGTYEC  LKYEKDAFKREHLAEVT SVKA
hCD86    IK DKGLYQC  HKKPTGMIRIHQMNSE SVLA
hB7-H1   LQ DAGVYRC  STGGADYKRITVKVNAP NEIN
mB7-H1   LQ DAGVYC C  SYGGADYKRITLKVNAP RKIN
hB7-H2   PQ DRQKFHC  LSQS.LGFQEVLSVEVT HVAA
hB7-H3   VA EGSFTC   SIRDFGSAAVSLQVAAP SKPS
hB7-DC   VR DEGQYQC  IYGV.AWDYKYLTLEVK SYRK
mB7-DC   VR DSGQYRC  ICGA.AWDYKYLTVEVK SYMR
hB7-H4   LT DAGTYKC  ITSKGKGNANLEYKTGAF SMPE
mB7-H4   LT DAGTYTC  RTSKGKGNANLEYKTGAF SKPE
hB7-H5   LL DSGLYC C  VEIRHHHSEHRVHGAME QVQT
mB7-H5   PR DSGLYC C  IELKNHHPEQRFYGSME QVQA
              130            140           150
```

```
           15                  30                    45
ATGGGCGTCCCCACGGCCCTGGAGGCCGGCAGCTGGCGCTGGGGA
 M   G   V   P   T   A   L   E   A   G   S   W   R   W   G>

60                  75                    90
TCCCTGCTCTTCGCTCTCTTCCTGGCTGCGTCCCTAGGTCCGGTG
 S   L   L   F   A   L   F   L   A   A   S   L   G   P   V>

105                 120                   135
GCAGCCTTCAAGGTCGCCACGCCGTATTCCCTGTATGTCTGTCCC
 A   A   F   K   V   A   T   P   Y   S   L   Y   V   C   P>

150                 165                   180
GAGGGGCAGAACGTCACCCTCACCTGCAGGCTCTTGGGCCCTGTG
 E   G   Q   N   V   T   L   T   C   R   L   L   G   P   V>

195                 210                   225
GACAAAGGGCACGATGTGACCTTCTACAAGACGTGGTACCGCAGC
 D   K   G   H   D   V   T   F   Y   K   T   W   Y   R   S>

240                 255                   270
TCGAGGGGCGAGGTGCAGACCTGCTCAGAGCGCCGGCCCATCCGC
 S   R   G   E   V   Q   T   C   S   E   R   R   P   I   R>

285                 300                   315
AACCTCACGTTCCAGGACCTTCACCTGCACCATGGAGGCCACCAG
 N   L   T   F   Q   D   L   H   L   H   H   G   G   H   Q>

330                 345                   360
GCTGCCAACACCAGCCACGACCTGGCTCAGCGCCACGGGCTGGAG
 A   A   N   T   S   H   D   L   A   Q   R   H   G   L   E>

375                 390                   405
TCGGCCTCCGACCACCATGGCAACTTCTCCATCACCATGCGCAAC
 S   A   S   D   H   H   G   N   F   S   I   T   M   R   N>

420                 435                   450
CTGACCCTGCTGGATAGCGGCCTCTACTGCTGCCTGGTGGTGGAG
 L   T   L   L   D   S   G   L   Y   C   C   L   V   V   E>

465                 480                   495
ATCAGGCACCACCACTCGGAGCACAGGGTCCATGGTGCCATGGAG
 I   R   H   H   H   S   E   H   R   V   H   G   A   M   E>

510                 525                   540
CTGCAGGTGCAGACAGGCAAAGATGCACCATCCAACTGTGTGGTG
 L   Q   V   Q   T   G   K   D   A   P   S   N   C   V   V>

555                 570                   585
TACCCATCCTCCTCCCAGGAGAGTGAAAACATCACGGCTGCAGCC
 Y   P   S   S   S   Q   E   S   E   N   I   T   A   A   A>
```

Fig. 9A                                    (SEQ ID NO: 2)

```
                    600            615            630
         CTGGCTACGGGTGCCTGCATCGTAGGAATCCTCTGCCTCCCCCTC
          L  A  T  G  A  C  I  V  G  I  L  C  L  P  L>

645            660            675
         ATCCTGCTCCTGGTCTACAAGCAAAGGCAGGCAGCCTCCAACCGC
          I  L  L  L  V  Y  K  Q  R  Q  A  A  S  N  R>

690            705            720
         CGTGCCCAGGAGCTGGTGCGGATGGACAGCAACATTCAAGGGATT
          R  A  Q  E  L  V  R  M  D  S  N  I  Q  G  I>

735            750            765
         GAAAACCCCGGCTTTGAAGCCTCACCACCTGCCCAGGGGATACCC
          E  N  P  G  F  E  A  S  P  P  A  Q  G  I  P>

780            795            810
         GAGGCCAAAGTCAGGCACCCCCTGTCCTATGTGGCCCAGCGGCAG
          E  A  K  V  R  H  P  L  S  Y  V  A  Q  R  Q>

825            840            855
         CCTTCTGAGTCTGGGCGGCATCTGCTTTCGGAGCCCAGCACCCCC
          P  S  E  S  G  R  H  L  L  S  E  P  S  T  P>

870            885            900
         CTGTCTCCTCCAGGCCCCGGAGACGTCTTCTTCCCATCCCTGGAC
          L  S  P  P  G  P  G  D  V  F  F  P  S  L  D>

915            930
         CCTGTCCCTGACTCTCCAAACTTTGAGGTCATCTAG
          P  V  P  D  S  P  N  F  E  V  I  *>

(SEQ ID NO: 2)
```

Fig. 9B

```
         15                   30                   45
ATGGGTGTCCCCGCGGTCCCAGAGGCCAGCAGCCCGCGCTGGGGA
 M  G  V  P  A  V  P  E  A  S  S  P  R  W  G>

60                   75                   90
ACCCTGCTCCTTGCTATTTTCCTGGCTGCATCCAGAGGTCTGGTA
 T  L  L  A  I  F  L  A  A  S  R  G  L  V>

105                  120                  135
GCAGCCTTCAAGGTCACCACTCCATATTCTCTCTATGTGTGTCCC
 A  A  F  K  V  T  T  P  Y  S  L  Y  V  C  P>

150                  165                  180
GAGGGACAGAATGCCACCCTCACCTGCAGGATTCTGGGCCCCGTG
 E  G  Q  N  A  T  L  T  C  R  I  L  G  P  V>

195                  210                  225
TCCAAAGGGCACGATGTGACCATCTACAAGACGTGGTACCTCAGC
 S  K  G  H  D  V  T  I  Y  K  T  W  Y  L  S>

240                  255                  270
TCACGAGGCGAGGTCCAGATGTGCAAAGAACACCGGCCCATACGC
 S  R  G  E  V  Q  M  C  K  E  H  R  P  I  R>

285                  300                  315
AACTTCACATTGCAGCACCTTCAGCACCACGGAAGCCACCTGAAA
 N  F  T  L  Q  H  L  Q  H  H  G  S  H  L  K>

330                  345                  360
GCCAACGCCAGCCATGACCAGCCCCAGAAGCATGGGCTAGAGCTA
 A  N  A  S  H  D  Q  P  Q  K  H  G  L  E  L>

375                  390                  405
GCTTCTGACCACCACGGTAACTTCTCTATCACCCTGCGCAATGTG
 A  S  D  H  H  G  N  F  S  I  T  L  R  N  V>

420                  435                  450
ACCCCAAGGGACAGCGGCCTCTACTGCTGTCTAGTGATAGAATTA
 T  P  R  D  S  G  L  Y  C  C  L  V  I  E  L>

465                  480                  495
AAAAACCACCACCCAGAACAACGGTTCTACGGGTCCATGGAGCTA
 K  N  H  H  P  E  Q  R  F  Y  G  S  M  E  L>

510                  525                  540
CAGGTACAGGCAGGCAAAGGCTCGGGGTCCACATGCATGGCGTCT
 Q  V  Q  A  G  K  G  S  G  S  T  C  M  A  S>

555                  570                  585
AATGAGCAGGACAGTGACAGCATCACGGCTGCGGCCCTGGCCACC
 N  E  Q  D  S  D  S  I  T  A  A  A  L  A  T>
```

Fig. 10A                                    (SEQ ID NO: 4)

```
              600            615            630
GGCGCCTGCATCGTGGGAATCCTCTGCCTCCCCCTTATCCTGCTG
 G  A  C  I  V  G  I  L  C  L  P  I  L  L >

645            660            675
CTGGTCTATAAGCAGAGACAGGTGGCCTCTCACCGCCGTGCCCAG
 L  V  Y  K  Q  R  Q  V  A  S  H  R  R  A  Q >

690            705            720
GAGTTGGTGAGGATGGACAGCAGCAACACCCAAGGAATCGAAAAC
 E  L  V  R  M  D  S  S  N  T  Q  G  I  E  N >

735            750            765
CCAGGCTTCGAGACCACTCCACCCTTCCAGGGGATGCCTGAGGCC
 P  G  F  E  T  T  P  P  F  Q  G  M  P  E  A >

780            795            810
AAGACCAGGCCGCCACTGTCCTATGTGGCCCAGCGGCAACCTTCG
 K  T  R  P  P  L  S  Y  V  A  Q  R  Q  P  S >

825            840            855
GAGTCAGGACGGTACCTGCTCTCTGACCCCAGCACACCTCTGTCG
 E  S  G  R  Y  L  L  S  D  P  S  T  P  L  S >

870            885            900
CCTCCAGGCCCTGGGGACGTCTTTTTCCCATCCCTAGATCCAGTC
 P  P  G  P  G  D  V  F  F  P  S  L  D  P  V >

915            930
CCTGACTCCCCTAACTCTGAAGCCATCTAA
 P  D  S  P  N  S  E  A  I  * >
                              (SEQ ID NO: 4)
```

Fig. 10B

B7-H5, A COSTIMULATORY POLYPEPTIDE

CROSS REFERENCE TO RELATED APPLICATIONS

This application is a national phase filing under 35 U.S.C. §371 of international application number PCT/US2005/022321, filed Jun. 24, 2005, which claims the benefit of priority of U.S. provisional application No. 60/582,491 filed Jun. 24, 2004. The disclosures of the prior applications are considered part of (and are incorporated by reference in) the disclosure of this application.

BACKGROUND

Activated T lymphocytes play critical roles in host defense against viral infection and cancer and are involved in the progression of autoimmune diseases. Two distinct signals are typically required for optimal activation of antigen-specific T lymphocytes. The first signal is provided by the interactions of the complex of antigenic peptide and major histocompatibility complex (MHC) with the T cell receptor (TCR). The second signal is delivered to T cells by costimulatory molecules expressed on antigen-presenting cells (APCs). Studies have demonstrated that costimulatory interactions stimulate T cell growth, up-regulate cytokine production, and promote T cell differentiation. Furthermore, ligation of costimulatory molecules provides a survival signal essential for T cells to prevent apoptosis. In addition, costimulatory signals appear to be critical for the induction and maintenance of T cell anergy. More importantly, there is clear interest in therapeutic manipulation of costimulatory pathways because the control of costimulatory signals can provide a means either to enhance or to inhibit immune responses.

SUMMARY

The invention is based, in part, on the cloning of human and mouse cDNA molecules encoding novel homologous molecules that co-stimulate the T cell responses of both species and on the functional characterization of the polypeptides that the cDNA molecules encode. The human polypeptide is designated hB7-H5 and the mouse polypeptide mB7-H5. Text that refers to B7-H5 without specifying human versus mouse is pertinent to both forms of B7-H5. The invention features DNA molecules encoding the hB7-H5, mB7-H5 polypeptides, functional fragments of the polypeptides, and fusion proteins containing the polypeptides or functional fragments of the polypeptides, hB7-H5 and mB7-H5 and functional fragments of both, vectors containing the DNA molecules, and cells containing the vectors. Also included in the invention are antibodies that bind to the B7-H5 polypeptides. The invention features in vitro, in vivo, and ex vivo methods of co-stimulating T cell responses, methods of screening for compounds that inhibit or enhance T cell responses, and methods for producing the above polypeptides and fusion proteins.

Specifically the invention features an isolated nucleic acid (e.g., a DNA) including: (a) a nucleic acid sequence that (i) encodes a B7-H5 polypeptide with the ability to co-stimulate a T cell, and (ii) hybridizes under highly stringent conditions to the complement of SEQ ID NO:2 or SEQ ID NO:4 or to the complement of a sequence that encodes a polypeptide with an amino acid sequence with SEQ ID NO:1 or SEQ ID NO:3; or (b) a complement of this nucleic acid sequence. The nucleic acid sequence included in the isolated DNA will be at least 10 bp, 15 bp, 25 bp, 50 bp, 75 bp, 100 bp, 125 bp, 150 bp, 175 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 910 bp, 915 bp, 920 bp, 925 bp, 926 bp, 927 bp, 928 bp, 929 bp, 930 bp, 931 bp, 932 bp, or 933 bp long. The nucleic acid sequence can encode a B7-H5 polypeptide that includes an amino sequence with SEQ ID NO:1 or SEQ 1D NO:3 with up to 20 (e.g., 0, 2, 5, 10, or 15) amino acid insertions, deletions, or substitutions, or it can have a nucleotide sequence that includes SEQ ID NO:2 or SEQ ID NO:4. The nucleic acid sequence can also encode functional fragments of these B7-H5 polypeptides, e.g., fragments with the ability to co-stimulate a T cell.

The invention also embodies an isolated B7-H5 polypeptide, e.g., a polypeptide encoded by a DNA that includes a nucleic acid sequence that (i) encodes a polypeptide with the ability to co-stimulate a T cell and (ii) hybridizes under stringent conditions to the complement of a sequence that encodes a polypeptide with an amino acid sequence with SEQ ID NO:1 or SEQ ID NO:3. The B7-H5 polypeptide can include an amino sequence of amino acid residue 20, 21, 22, 23, 24, 25, 26, 27, 28, 29, 30, 31, 32, 33, 34, 35, 36, 37, 38, 39, or 40 to amino acid residue 311 of SEQ ID NO:1 or amino acid residue 309 of SEQ ID NO:3. The invention also encompasses B7-H5 polypeptides that include an amino acid sequence with SEQ ID NO:1 or SEQ ID NO:3, or either of these amino acid sequences but differing solely by not more than 20 (e.g., not more than 15, 10, 5, 2, or 1) conservative substitutions or by not more than 20 (e.g., not more than 15, 10, 5, 2, or 1) amino acid insertions, deletions, or substitutions, and further encompasses functional fragments of any of these polypeptides, e.g., a fragment that has the ability to co-stimulate a T cell. Also included are isolated immunogenic polypeptides comprising at least 8 (e.g., 10, 15, 20, 25, 30, 40, or 50) consecutive residues of the polypeptides disclosed herein. The polypeptides of the invention include fusion proteins containing a first domain and at least one additional domain. The first domain can be any of the B7-H5 polypeptides described above or a functional fragment of any of these polypeptides. The at least one additional domain can be, for example, a heterologous targeting or leader sequence, or an amino acid sequence that facilitates purification, detection, or solubility of the fusion protein. The second domain can be, for example, all or part of an immunoglobulin (Ig) heavy chain constant region. Also included are isolated nucleic acid molecules encoding the fusion proteins.

The invention features vectors containing any of the nucleic acids of the invention and nucleic acid molecules encoding the fusion proteins of the invention. The vectors can be expression vectors in which the nucleic acid coding sequence or molecule is operably linked to an expression control sequence, e.g., a regulatory element that allows expression of the nucleic acid sequence or molecule in a cell. Also included in the invention are cells (e.g., mammalian, insect, yeast, fungal, or bacterial cells) containing any of the vectors of the invention.

Another embodiment of the invention is a method of co-stimulating a T cell that involves contacting the T cell with any of the B7-H5 polypeptides of the invention, functional fragments thereof, or fusion proteins of the invention; these 3 classes of molecule are, for convenience, designated "B7-H5 agents." The contacting can be by culturing any of these B7-H5 agents with the T cell in vitro. Alternatively, the T cell can be in a mammal (e.g., a human, non-human primate (e.g., monkey), mouse, rat, guinea pig, cow, sheep, horse, pig, rabbit, dog, or cat) and the contacting can be, for example, by administering any of the B7-H5 agents to the mammal or administering a nucleic acid encoding the B7-H5 agent to the mammal. In addition, the method can be an ex vivo procedure that involves providing a recombinant cell which is the progeny of a cell obtained from the mammal and has been transfected or transformed ex vivo with a nucleic acid encoding any of the B7-H5 agents so that the cell expresses the B7-H5 agent; and administering the cell to the mammal. In this ex vivo procedure, the cell can be an antigen presenting cell (APC) that expresses the B7-H5 agent on its surface. Furthermore, prior to administering to the mammal, the APC can be pulsed with an antigen or an antigenic peptide. In any of the above methods, the mammal can be suspected of having, for example, an immunodeficiency disease, an inflammatory condition, or an autoimmune disease. In addition, in any of the methods, the T cell can be a helper T cell, e.g., a T cell that helps an effector (e.g., a cytotoxic T lymphocyte (CTL) or B cell antibody) response. An antibody response can be, for example, an IgM, IgG1, IgG2a, IgG2b, IgG3, IgG4, IgE, or IgA antibody response. Co-stimulation of a T cell by any of the B7-H5 agents can result in an increase in the level of CD40 ligand on the surface of the T cell.

The invention includes a method of identifying a compound that inhibits an immune response. The method involves: providing a test compound; culturing, together, the compound, one or more B7-H5 agents, a T cell, and a T cell activating stimulus; and determining whether the test compound inhibits the response of the T cell to the stimulus, as an indication that the test compound inhibits an immune response. The invention also embodies a method of identifying a compound that enhances an immune response. The method involves: providing a test compound; culturing, together, the compound, one or more of B7-H5 agents, a T cell, and a T cell activating stimulus; and determining whether the test compound enhances the response of the T cell to the stimulus, as an indication that the test compound enhances an immune response. In both these methods, the stimulus can be, for example, an antibody that binds to a T cell receptor or a CD3 polypeptide. Alternatively, the stimulus can be an alloantigen or an antigenic peptide bound to a major histocompatibility complex (MHC) molecule on the surface of an antigen presenting cell (APC). The APC can be transfected or transformed with a nucleic acid encoding the B7-H5 agent and the B7-H5 agent can be expressed on the surface of the APC.

The invention also features an antibody (e.g., a polyclonal or a monoclonal antibody) that binds to any of the B7-H5 polypeptides of the invention, e.g., the polypeptide with SEQ ID NO:1 or SEQ ID NO:3, e.g., the 5H9 or the 1H11 monoclonal antibody disclosed herein. The invention also provides hybridomas secreting such monoclonal antibodies.

The invention also features a method of producing any of the B7-H5 polypeptides of the invention, functional fragments thereof, or fusion proteins of the invention. The method involves culturing a cell of the invention and purifying the relevant B7-H5 protein from the culture.

"Polypeptide" and "protein" are used interchangeably and mean any peptide-linked chain of amino acids, regardless of length or post-translational modification. The invention also features B7-H5 polypeptides with conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The term "isolated" polypeptide or peptide fragment as used herein refers to a polypeptide or a peptide fragment which either has no naturally-occurring counterpart (e.g., a peptidomimetic), or has been separated or purified from components which naturally accompany it, e.g., in tissues such as pancreas, liver, spleen, ovary, testis, muscle, joint tissue, neural tissue, gastrointestinal tissue, or body fluids such as blood, serum, or urine. Typically, the polypeptide or peptide fragment is considered "isolated" when it is at least 70%, by dry weight, free from the proteins and naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most preferably at least 99%, by dry weight, polypeptide x. Since a polypeptide that is chemically synthesized is, by its nature, separated from the components that naturally accompany it, the synthetic polypeptide or nucleic acid is "isolated."

An isolated polypeptide (or peptide fragment) of the invention can be obtained, for example, by extraction from a natural source (e.g., from human tissues or bodily fluids); by expression of a recombinant nucleic acid encoding the peptide; or by chemical synthesis. A peptide that is produced in a cellular system different from the source from which it naturally originates is "isolated," because it will be separated from components which naturally accompany it. The extent of isolation or purity can be measured by any appropriate method, e.g., column chromatography, polyacrylamide gel electrophoresis, or HPLC analysis.

An "isolated DNA" means DNA free of one or both of the genes that flank the gene containing the DNA of interest in the genome of the organism in which the gene containing the DNA of interest naturally occurs. The term therefore includes a recombinant DNA incorporated into a vector, into an autonomously replicating plasmid or virus, or into the genomic DNA of a prokaryote or eukaryote. It also includes a separate molecule such as: a cDNA where the corresponding genomic DNA has introns and therefore a different sequence; a genomic fragment; a fragment produced by polymerase chain reaction (PCR); a restriction fragment; a DNA encoding a non-naturally occurring protein, fusion protein, or fragment of a given protein; or a nucleic acid which is a degenerate variant of a naturally occurring nucleic acid. In addition, it includes a recombinant nucleotide sequence that is part of a hybrid gene, i.e., a gene encoding a fusion protein. Also included is a recombinant DNA that includes a portion of SEQ ID NO:2, SEQ ID NO:4, SEQ ID NO:5, or SEQ ID NO:6. It will be apparent from the foregoing that isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice.

As used herein, a polypeptide that "co-stimulates" a T cell is a polypeptide that, upon interaction with a cell-surface molecule on the T cell, enhances the response of the T cell. The T cell response that results from the interaction will be greater than the response in the absence of the polypeptide. The response of the T cell in the absence of the co-stimulatory polypeptide can be no response or it can be a response significantly lower than in the presence of the co-stimulatory polypeptide. It is understood that the response of the T cell can be an effector (e.g., CTL or antibody-producing B cell) response, a helper response providing help for one or more effector (e.g., CTL or antibody-producing B cell) responses, or a suppressive response.

As used herein, an "activating stimulus" is a molecule that delivers an activating signal to a T cell, preferably through the antigen specific T cell receptor (TCR). The activating stimulus can be sufficient to elicit a detectable response in the T cell. Alternatively, the T cell may require co-stimulation (e.g., by a B7-H5 polypeptide) in order to respond detectably to the activating stimulus. Examples of activating stimuli include, without limitation, antibodies that bind to the TCR or to a polypeptide of the CD3 complex that is physically associated with the TCR on the T cell surface, alloantigens, or an antigenic peptide bound to a MHC molecule.

As used herein, a "fragment" of a B7-H5 polypeptide is a fragment of the polypeptide that is shorter than the full-length, immature polypeptide. Generally, fragments will be 5 or more amino acids, e.g., 6, 7, 8, 9, 10, 12, 15, 18, 21, 25, 30, 35, 40, 50, 60, 80, 100, 120, 150, 180, 210, 240, 260, 270, 280, 285, 290, 295, 300, 303, 306, or 308 or more amino acids, in length. An antigenic fragment has the ability to be recognized and bound by an antibody. In certain embodiments, antigenic fragments are also functional fragments.

As used herein, a "functional fragment" of a B7-H5 polypeptide is a fragment of the polypeptide that is shorter than the full-length, immature polypeptide and has at least 25% (e.g., at least 30%, 40%, 50%, 60%, 70%, 80%, 90%, 95%, 98%, 99%, or even 100% or more) of the ability of the full-length mature B7-H5 polypeptide to co-stimulate a T cell. Methods of establishing whether a fragment of an B7-H5 molecule is functional are known in the art. For example, fragments of interest can be made by either recombinant, synthetic, or proteolytic digestive methods. Such fragments can then be isolated and tested for their ability to co-stimulate T cells by procedures described herein.

As used herein, "operably linked" means incorporated into a genetic construct so that expression control sequences effectively control expression of a coding sequence of interest.

As used herein, the term "antibody" refers not only to whole antibody molecules, but also to antigen-binding fragments, e.g., Fab, F(ab')2, Fv, and single chain Fv fragments. Also included are chimeric antibodies.

As used herein, an antibody that "binds specifically" to an isolated B7-H5 polypeptide encoded by a DNA that includes a nucleic acid sequence that (i) encodes a polypeptide with the ability to co-stimulate a T cell and (ii) hybridizes under stringent conditions to the complement of a sequence that encodes a polypeptide with an amino acid sequence with SEQ ID NO:1 or SEQ ID NO:3, is an antibody that does not bind to B7-1, B7-2, B7-H1, B7-H2, B7-H3, or B7H-4 polypeptides.

Unless otherwise defined, all technical and, scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., enhancing immune responses in mammalian subjects, will be apparent from the following description, from the drawings and from the claims.

DESCRIPTION OF DRAWINGS

FIG. 1 is a nucleotide sequence (SEQ ID NO:5) of a cDNA clone that includes a sequence encoding a human B7-H5 polypeptide. The B7-H5 start codon is indicated by bold and underscore. The B7-H5 stop codon is indicated by underscore.

FIG. 2 is a nucleotide sequence (SEQ ID NO:6) that includes a sequence encoding a mouse B7-H5 polypeptide. The B7-H5 start codon is indicated by bold and underscore. The B7-H5 stop codon is indicated by underscore.

FIG. 3 is an annotated amino acid sequence (SEQ ID NO:1) of human B7-H5. The IgV-like domain is underlined; a predicted intermolecular cysteine is indicated in bold and underscore; the predicted transmembrane domain is indicated in bold; a tyrosine that is potentially subject to phosphorylation is boxed.

FIG. 4 is an annotated amino acid sequence (SEQ ID NO:3) of mouse B7-H5. The IgV-like domain is underlined; a predicted intermolecular cysteine is indicated by bold and underscore; the predicted transmembrane domain is indicated in bold; tyrosines that are potentially subject to phosphorylation are boxed.

FIG. 6 is a structure-based alignment of B7-H5 and other B7 family members. Aligned are the amino acid sequences of segments of the B7 family (h: human, m: mouse) polypeptides (including B7-H5) that contain immunoglobulin superfamily (IgSF) V-domain sequences. IgSF V-set consensus residues are shown on a black background. Consensus residue positions are labeled with invariant IgSF residues or conserved residue character (h: hydrophobic, p: polar). Residue positions shown on a gray background are signature residues of the B7 family outside IgSF consensus positions. Beta-strands of the V-domain are designated according to IgSF conventions (A', B, C, C', C", D, F, G). Residue positions labeled with # are involved in dimerization of CD80/CD86 in their crystal structures and residues labeled with asterisks participate in CTLA4 binding. The amino acid sequences of the hCD80, hCD86, hB7-H1, mB7-H1, hB7-H2, hB7-H3, hB7-DC, mB7-DC, hB7-H4, mB7-H4, hB7-H5, and mB7-H5 segments are set forth herein as SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, respectively.

FIG. 9 is a translated nucleotide sequence (SEQ ID NO:2) of a cDNA encoding human B7-H5.

FIG. 10 is a translated nucleotide sequence (SEQ ID NO:4) of a cDNA encoding mouse B7-H5.

DETAILED DESCRIPTION

Figure 5:
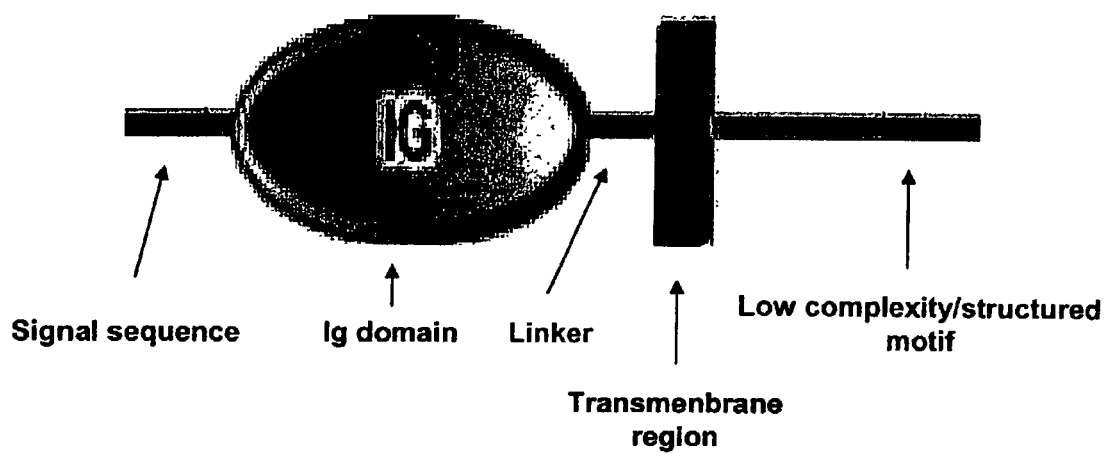
FIG. 5 is a representation of the domain structure of human B7-H5. A predicted signal sequence includes residues 1-29 of SEQ ID NO:1. A predicted immunoglobulin-like (Ig) domain includes residues 30-170 of SEQ ID NO:1. A predicted linker domain includes residues 171-194 of SEQ ID NO:1. A predicted transmembrane domain includes residues 195-216 of SEQ ID NO:1. Residues 217-311 form a predicted intracellular domain, with residues 280-292 forming a low complexity/structured motif. The domain structure and topology are conserved between the human and mouse B7-H5 polypeptides.

The applicants have discovered, inter alia, a new member of the B7 family of costimulatory molecules, which has been designated B7-H5. Both the human and mouse B7-H5 polypeptides and nucleotides encoding them are disclosed. Similar to other members of the B7 family, these B7-H5 polypeptides can co-stimulate T cells.

Nucleic Acid Molecules

The B7-H5 nucleic acid molecules of the invention can be cDNA, genomic DNA, synthetic DNA, or RNA, and can be double-stranded or single-stranded (i.e., either a sense or an antisense strand or both). Fragments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions.

The nucleic acid molecules of the invention can contain naturally occurring sequences, or sequences that differ from those that occur naturally, but, due to the degeneracy of the genetic code, encode the same polypeptide (for example, the polypeptides with SEQ ID NOs:1 or 3). In addition, these nucleic acid molecules are not limited to coding sequences, e.g., they can include some or all of the non-coding sequences that lie upstream or downstream from a coding sequence.

Nucleic acids of the invention can be nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

The nucleic acid molecules of the invention can be synthesized (for example, by phosphoramidite-based synthesis) or obtained from a biological cell, such as the cell of a mammal. Thus, the nucleic acids can be those of a human, non-human primate (e.g., monkey) mouse, rat, guinea pig, cow, sheep, horse, pig, rabbit, dog, or cat.

In addition, the isolated nucleic acid molecules of the invention encompass segments that are not found as such in the natural state. Thus, the invention encompasses recombinant nucleic acid molecules (for example, isolated nucleic acid molecules encoding B7-H5) incorporated into a vector (for example, a plasmid or viral vector) or into the genome of a heterologous cell or into the genome of a homologous cell at a position other than the natural chromosomal location. Recombinant nucleic acid molecules and uses therefor are discussed further below.

Certain nucleic acid molecules of the invention are antisense molecules or are transcribed into antisense molecules. These can be used, for example, to down-regulate translation of B7-H5 mRNA within a cell. Techniques associated with detection or regulation of genes are well known to skilled artisans and such techniques can be used to diagnose and/or treat disorders associated with aberrant B7-H5 expression. Nucleic acid molecules of the invention are discussed further below in the context of their therapeutic utility.

A B7-H5 family gene or protein can be identified based on its similarity to the relevant B7-H5 gene or protein, respectively. For example, the identification can be based on sequence identity. The invention features isolated nucleic acid molecules which are identical to, or are at least 50% (or 55%, 65%, 75%, 85%, 95%, or 98%) identical to: (a) a nucleic acid molecule that encodes the polypeptide of SEQ ID NO:1 or SEQ ID NO:3; (b) the nucleotide sequence of SEQ ID NO:2 or SEQ ID NO:4; or (c) a nucleic acid molecule which includes a segment of at least 10 (e.g., at least 15, 25, 50, 75, 100, 125, 150, 175, 200, 250, 300, 350, 400, 450, 500, 550, 600, 650, 700, 750, 800, 850, 900, 910, 915, 920, 925, 926, 927, 928, 929, 930, 931, 932, or 933) nucleotides of SEQ ID NO:2 or SEQ ID NO:4.

The determination of percent identity between two sequences is accomplished using the mathematical algorithm of Karlin and Altschul, *Proc. Natl. Acad. Sci. USA* 90, 5873-5877, 1993. Such an algorithm is incorporated into the BLASTN and BLASTP programs of Altschul et al. (1990) *J. Mol. Biol.* 215, 403-410. BLAST nucleotide searches are performed with the BLASTN program, score=100, wordlength=12 to obtain nucleotide sequences homologous to B7-H5-encoding nucleic acids. BLAST protein searches are performed with the BLASTP program, score=50, wordlength=3 to obtain amino acid sequences homologous to B7-H5. To obtain gapped alignments for comparative purposes, Gapped BLAST is utilized as described in Altschul et al. (1997) *Nucleic Acids Res.* 25, 3389-3402. When utilizing BLAST and Gapped BLAST programs, the default parameters of the respective programs (e.g., XBLAST and NBLAST) are used (see ncbi.nlm.nih.gov).

Hybridization can also be used as a measure of homology between two nucleic acid sequences. A B7-H5-encoding nucleic acid sequence, or a portion thereof, can be used as hybridization probe according to standard hybridization techniques. The hybridization of a B7-H5 probe to DNA from a test source (e.g., a mammalian cell) is an indication of the presence of B7-H5 DNA in the test source. Hybridization conditions are known to those skilled in the art and can be found in *Current Protocols in Molecular Biology*, John Wiley & Sons, N.Y., 6.3.1-6.3.6, 1991. Moderate hybridization conditions are defined as equivalent to hybridization in 2× sodium chloride/sodium citrate (SSC) at 30° C., followed by one or more washes in 1×SSC, 0.1% SDS at 50-60° C. Highly stringent conditions are defined as equivalent to hybridization in 6× sodium chloride/sodium citrate (SSC) at 45° C., followed by one or more washes in 0.2×SSC, 0.1% SDS at 50-65° C.

The invention also encompasses: (a) vectors that contain any of the foregoing B7-H5-related coding sequences and/or their complements (that is, "antisense" sequence); (b) expression vectors that contain any of the foregoing B7-H5-related coding sequences operatively linked to one or more transcriptional/translational regulatory elements (examples of which are given below) that direct expression of the coding sequences; (c) expression vectors containing, in addition to sequences encoding a B7-H5 polypeptide, nucleic acid sequences that are unrelated to nucleic acid sequences encoding B7-H5, such as molecules encoding a reporter, marker, or a signal peptide, e.g., fused to B7-H5; and (d) genetically engineered host cells that contain any of the foregoing expression vectors and thereby express the nucleic acid molecules of the invention.

Recombinant nucleic acid molecules can contain a sequence encoding B7-H5 having a heterologous signal sequence. The full length B7-H5 polypeptide, a domain of B7-H5, or a fragment thereof may be fused to additional polypeptides, as described below. Similarly, the nucleic acid molecules of the invention can encode the mature form of B7-H5 or a form that includes an exogenous polypeptide that facilitates secretion.

The transcriptional/translational regulatory elements referred to above and which are further described below, include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase ($neo^r$, $G418^r$), dihydrofolate reductase (DHFR), hygromycin-B-phosphotransferase (HPH), thymidine kinase (TK), lacZ (encoding β-galactosidase), and xanthine guanine phosphoribosyltransferase (XG-PRT). As with many of the standard procedures associated with the practice of the invention, skilled artisans will be aware of additional useful reagents, for example, additional sequences that can serve the function of a marker or reporter. Generally, the hybrid polypeptide will include a first portion and a second portion; the first portion being a B7-H5 polypeptide (or any of the fragment of such a polypeptide disclosed herein) and the second portion being, for example, the reporter described above or an Ig constant region or part of an Ig constant region, e.g., the CH2 and CH3 domains of IgG2a.

The expression systems that may be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecules of the invention, preferably containing a nucleic acid sequence (e.g., SEQ ID NO:2 or 4) encoding a B7-H5 polypeptide; insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing B7-H5 nucleotide sequences; or mammalian cell systems (for example, COS, CHO, BHK, 293, VERO, HeLa, MDCK, W138, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal transfected with a plasmid vector or infected with a viral vector.

A host cell (e.g., a prokaryotic cell or a eukaryotic cell such as a COS cell) can be used to, for example, produce the costimulatory polypeptides provided herein. In some embodiments, a host cell (e.g., an APC) can be used to express the costimulatory polypeptides of the invention for presentation to a T cell.

Polypeptides and Polypeptide Fragments

The polypeptides of the invention include B7-H5 and functional fragments thereof. The polypeptides disclosed herein also include fusion proteins which contain either full-length B7-H5 or a functional fragment thereof fused to an unrelated amino acid sequence. The unrelated sequences can be additional functional domains or signal peptides. Signal peptides are described in greater detail and exemplified below. The polypeptides can also be any of those described above but with one or more conservative substitutions.

The polypeptides can be purified from natural sources (e.g., blood, serum plasma, tissues, or cells such as T cells or any cell that naturally produces B7-H5). Polypeptides can also be conveniently synthesized by standard chemical means. In addition, polypeptides can be produced by standard in vitro recombinant DNA techniques and in vivo recombination/genetic recombination (e.g., transgenesis), using the nucleotide sequences encoding the appropriate polypeptides. Methods well known to those skilled in the art can be used to construct expression vectors containing relevant coding sequences and appropriate transcriptional/translational control signals. See, for example, the techniques described in Sambrook et al., *Molecular Cloning: A Laboratory Manual* (2nd Ed.) (Cold Spring Harbor Laboratory, N.Y., 1989), and Ausubel et al., *Current Protocols in Molecular Biology*, (Green Publishing Associates and Wiley Interscience, N.Y., 1989).

Polypeptides and fragments of the invention also include those described above, but modified for in vivo use by the addition, the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

B7-H5 polypeptides can be purified using, for example, chromatographic methods such as DEAE ion exchange, gel filtration, and hydroxyapatite chromatography. For example, a B7-H5 polypeptide in a cell culture supernatant or a cytoplasmic extract can be purified using a protein G column. In some embodiments, B7-H5 polypeptides can be "engineered" to contain an amino acid sequence that allows the polypeptides to be captured onto an affinity matrix. For example, a tag such as c-myc, glutathione S-transferase (GST), hemagglutinin, polyhistidine, or Flag™ (Kodak) can be used to aid polypeptide purification. Such tags can be inserted anywhere within the polypeptide, including at either the carboxyl or amino terminus. Immunoaffinity chromatography also can be used to purify costimulatory polypeptides.

Also of interest are peptidomimetic compounds that are designed based upon the amino acid sequences of the functional peptide fragments. Peptidomimetic compounds are synthetic compounds having a three-dimensional conformation (i.e., a "peptide motif") that is substantially the same as the three-dimensional conformnation of a selected peptide. The peptide motif provides the peptidomimetic compound with the ability to co-stimulate T cells in a manner qualitatively identical to that of the B7-H5 functional peptide fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Methods of Co-Stimulating a T Cell

The methods of the invention involve contacting a T cell with a B7-H5 polypeptide of the invention, or a functional fragment thereof, in order to co-stimulate the T cell. Such polypeptides or functional fragments can have amino acid sequences identical to wild-type sequences or they can contain one or more conservative substitutions. The contacting can occur before, during, or after activation of the T cell. Contacting of the T cell with the B7-H5 polypeptide will preferably be at substantially the same time as activation. Activation can be, for example, by exposing the T cell to an antibody that binds to the T cell receptor (TCR) or one of the polypeptides of the CD3 complex that is physically associated with the TCR. Alternatively, the T cell can be exposed to either an alloantigen (e.g., a major histocompatibility (MHC) alloantigen) on, for example, an antigen presenting cell (APC) (e.g., a dendritic cell, a macrophage, a monocyte, or a B cell) or an antigenic peptide produced by processing of a protein antigen by any of the above APC and presented to the T cell by MHC molecules on the surface of the APC. The T cell can be a CD4$^+$ T cell or a CD8$^+$ T cell. The B7-H5 polypeptide can be added to the solution containing the cells, or it can be expressed on the surface of an APC, e.g., an APC presenting an alloantigen or an antigen peptide bound to an MHC molecule. Alternatively, if the activation is in vitro, the B7-H5 polypeptide can be bound to a surface of the relevant culture vessel, e.g., a well of a plastic microtiter plate.

The methods can be performed in vitro, in vivo, or ex vivo. In vitro application of B7-H5 can be useful, for example, in basic scientific studies of immune mechanisms or for production of activated T cells for use in either studies on T cell function or, for example, passive immunotherapy. Furthermore, B7-H5 could be added to in vitro assays (e.g., in T cell proliferation assays) designed to test for immunity to an antigen of interest in a subject from which the T cells were obtained. Addition of B7-H5 to such assays would be expected to result in a more potent, and therefore more readily detectable, in vitro response. However, the methods of the invention will preferably be in vivo or ex vivo (see below).

The B7-H5 polypeptides and variants thereof are generally useful as immune response-stimulating therapeutics. For example, the polypeptides of the invention can be used for treatment of disease conditions characterized by immunosuppression: e.g., cancer, AIDS or AIDS-related complex, other virally or environmentally-induced conditions, and certain congenital immune deficiencies. The polypeptides may also be employed to increase immune function that has been impaired by the use of radiotherapy or immunosuppressive drugs such as certain chemotherapeutic agents, and therefore are particularly useful when given in conjunction with such drugs or radiotherapy. The polypeptides can, furthermore, be used to enhance immune responses in normal subjects.

These methods of the invention can be applied to a wide range of species, e.g., humans, non-human primates, horses, cattle, pigs, sheep, goats, dogs, cats, rabbits, guinea pigs, hamsters, rats, and mice.

In Vivo Approaches

In one in vivo approach, a B7-H5 polypeptide (or a functional fragment thereof) itself is administered to the subject. Generally, the compounds of the invention will be suspended in a pharmaceutically-acceptable carrier (e.g., physiological saline) and administered orally or by intravenous infusion, or injected subcutaneously, intramuscularly, intraperitoneally, intrarectally, intravaginally, intranasally, intragastrically, intratracheally, or intrapulmonarily. They are preferably delivered directly to an appropriate lymphoid tissue (e.g. spleen, lymph node, or mucosal-associated lymphoid tissue (MALT)). The dosage required depends on the choice of the route of administration, the nature of the formulation, the nature of the patient's illness, the subject's size, weight, surface area, age, and sex, other drugs being administered, and the judgment of the attending physician. Suitable dosages are in the range of 0.01-10 mg/kg. Wide variations in the needed dosage are to be expected in view of the variety of polypeptides and fragments available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, a polynucleotide containing a nucleic acid sequence encoding a B7-H5 polypeptide or functional fragment thereof can be delivered to an appropriate cell of the animal. Expression of the coding sequence will preferably be directed to lymphoid tissue of the subject by, for example, delivery of the polynucleotide to the lymphoid tissue. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 µm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis, i.e., larger than 5 µm and preferably larger than 20 µm.

Another way to achieve uptake of the nucleic acid is using liposomes, prepared by standard methods. The vectors described herein can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995), *J. Mol. Med.* 73, 479). Alternatively, lymphoid tissue specific targeting can be achieved by the use of lymphoid tissue-specific transcriptional regulatory elements (TRE) such as a B lymphocyte, T lymphocyte, or dendritic cell specific TRE. Lymphoid tissue specific TRE are known (Thompson et al. (1992), *Mol. Cell. Biol.* 12, 1043-1053; Todd et al. (1993), *J. Exp. Med.* 177, 1663-1674; Penix et al. (1993), *J. Exp. Med.* 178, 1483-1496). Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding a B7-H5 polypeptide or functional fragment of interest with an initiator methionine and optionally a targeting sequence is operatively linked to a promoter or enhancer-promoter combination.

Short amino acid sequences can act as signals to direct proteins to specific intracellular compartments. For example, hydrophobic signal peptides (e.g., MAISGVPVLGFFIIAVLMSAQESWA (SEQ ID NO:7)) are found at the amino terminus of proteins destined for the endoplasmic reticulum (ER). Whereas the sequence KFERQ (SEQ ID NO:8) and other closely related sequences are known to target intracellular polypeptides to lysosomes, other sequences (e.g., MDDQRDLISNNEQLP (SEQ ID NO:9) direct polypeptides to endosomes. In addition, the peptide sequence KDEL (SEQ ID NO:10) has been shown to act as a retention signal for the ER. Each of these signal peptides, or a combination thereof, can be used to traffic the B7-H5 polypeptides or functional fragments of the invention as desired. DNAs encoding the B7-H5 polypeptides or functional fragments containing targeting signals will be generated by PCR or other standard genetic engineering or synthetic techniques.

A promoter is a TRE composed of a region of a DNA molecule, typically within 100 base pairs upstream of the point at which transcription starts. Enhancers provide expression specificity in terms of time, location, and level. Unlike a promoter, an enhancer can function when located at variable distances from the transcription site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles which are suitable for administration to a human, e.g., physiological saline. A therapeutically effective amount is an amount of the polynucleotide which is capable of producing a medically desirable result (e.g., an enhanced T cell response) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

Included in these in vivo approaches, are methods of co-stimulating a T cell that involve administering more than one co-stimulatory molecule or functional fragment thereof. Such combinations can be any combination of one or more of co-stimulatory polypeptides, e.g., B7-1, B7-2, B7-H1, B7-H2, B7-H3, B7-H4, B7-H5, 4-1BB, OX40, or HVEM and functional fragments of any of these. The proteins or functional fragments per se can be administered or nucleic acids (e.g., expression vectors) encoding the proteins or functional fragments can be administered. Where expression vectors are used, a single vector containing coding sequences for two or more of the co-stimulatory polypeptides or functional fragments can be administered. Alternatively, multiple (e.g., 2, 3, 4, 5, or 6) individual vectors, each encoding one or more (e.g., 2, 3, 4, 5, or 6) of the co-stimulatory polypeptides or functional fragments thereof can be administered.

Ex Vivo Approaches

Peripheral blood mononuclear cells (PBMC) can be withdrawn from the patient or a suitable donor and exposed ex vivo to an activating stimulus (see above) and a B7-H5 polypeptide or polypeptide fragment (whether in soluble form or attached to a sold support by standard methodologies). The PBMC containing highly activated T cells are then introduced into the same or a different patient.

An alternative ex vivo strategy can involve transfecting or transducing cells obtained from the subject with a polynucleotide encoding a B7-H5 polypeptide or functional fragment-encoding nucleic acid sequences described above. The transfected or transduced cells are then returned to the subject. Such cells are preferably hematological cells (e.g., bone marrow cells, macrophages, monocytes, dendritic cells, or B cells), although they can also be any of a wide range of types including, without limitation, fibroblasts, epithelial cells, endothelial cells, keratinocytes, or muscle cells in which they act as a source of the B7-H5 polypeptide or functional fragment thereof for as long as they survive in the subject. The use of hematological cells that include the above APC would be particularly advantageous in that such cells would be expected to home to, among others, lymphoid tissue (e.g., lymph nodes or spleen) and thus the B7-H5 polypeptide or functional fragment would be produced in high concentration at the site where they exert their effect, i.e., enhancement of an immune response. In addition, if APC are used, the APC expressing the exogenous B7-H5 molecule can be the same APC that presents an alloantigen or antigenic peptide to the relevant T cell. The B7-H5 polypeptides can be secreted by the APC or expressed on its surface. Prior to returning the recombinant APC to the patient, they can optionally be exposed to sources of antigens or antigenic peptides of interest, e.g., those of tumors, infectious microorganisms, or autoantigens. The same genetic constructs and trafficking sequences described for the in vivo approach can be used for this ex vivo strategy. Furthermore, tumor cells, preferably obtained from a patient, can be transfected or transformed by a vector encoding a B7-H5 polypeptide or functional fragment thereof. The tumor cells, preferably treated with an agent (e.g., ionizing irradiation) that ablates their proliferative capacity, are then returned to the patient where, due to their expression of the exogenous B7-H5 polypeptides (on their cell surface or secreted), they can stimulate enhanced tumoricidal T cell immune responses. It is understood that the tumor cells that, after transfection or transformation, are injected into the patient, can also have been originally obtained from an individual other than the patient.

The ex vivo methods include the steps of harvesting cells from a subject, culturing the cells, transducing them with an expression vector, and maintaining the cells under conditions suitable for expression of the B7-H5 polypeptide or functional fragment. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are then selected, for example, for expression of the coding sequence or of a drug resistance gene. The cells may then be lethally irradiated (if desired) and injected or implanted into the patient.

It is understood that in these ex vivo procedures, the cells to be introduced into a subject can be transfected or transformed with one or more (e.g., two, three, four, five, or six) expression vectors containing one or more (e.g., two, three, four, five, or six) sequences encoding any of the co-stimulatory molecules listed above (e.g., B7-1, B7-2, B7-H1, B7-H2, B7-H3, B7-H4, or B7-H5) or functional fragments thereof prior to introduction.

Methods of Screening for Compounds that Inhibit or Enhance Immune Responses

The invention provides methods for testing compounds (small molecules or macromolecules) that inhibit or enhance an immune response. Such a method can involve, e.g., culturing a B7-H5 polypeptide of the invention (or a functional fragment thereof) with T cells in the presence of a T cell stimulus (see above). The B7-H5 molecule can be in solution or membrane bound (e.g., expressed on the surface of the T cells) and it can be natural or recombinant. Furthermore, the B7-H5 polypeptides (or functional fragments thereof) can have amino acid sequences identical to wild-type sequences or they can have one or more conservative substitutions. Compounds that inhibit the T cell response will likely be compounds that inhibit an immune response while those that enhance the T cell response will likely be compounds that enhance an immune response.

The invention also relates to using B7-H5 or functional fragments thereof to screen for immunomodulatory compounds that can interact with B7-H5. One of skill in the art would know how to use standard molecular modeling or other techniques to identify small molecules that would bind to T cell interactive sites of B7-H5. One such example is provided in Broughton (1997) *Curr. Opin. Chem. Biol.* 1, 392-398.

A candidate compound can modulate, e.g., inhibit or enhance, an immune response. A candidate compound that causes a requirement for at least 1.5-fold (e.g., 2-fold, 4-fold, 6-fold, 10-fold, 150-fold, 1000-fold, 10,000-fold, or 100,000-fold) more B7-H5 in order to achieve a defined arbitrary level of T cell activation than in the absence of the compound can be useful for inhibiting an immune response. On the other hand, a candidate compound that causes a requirement of at least 1.5 fold (e.g., 2-fold, 4-fold, 6-fold, 10-fold, 100-fold, 1000-fold, 10,000 fold, or 100,000-fold) less B7-H5 to achieve a defined arbitrary level of T cell activation than in the absence of the compound can be useful for enhancing an immune response. Compounds capable of interfering with or modulating B7-H5 function are good candidates for immunosuppressive immunoregulatory agents, e.g., to modulate an autoimmune response or suppress allogeneic or xenogeneic graft rejection.

B7-H5 Antibodies

The invention features antibodies that bind to the B7-H5 polypeptides or fragments of such polypeptides. Such antibodies can be polyclonal antibodies present in the serum or plasma of animals (e.g., mice, rabbits, rats, guinea pigs, sheep, horses, goats, cows, or pigs) which have been immunized with the relevant B7-H5 polypeptide or peptide fragment using methods, and optionally adjuvants, known in the art. Such polyclonal antibodies can be isolated from serum or plasma by methods known in the art. Monoclonal antibodies that bind to the above polypeptides or fragments are also embodied by the invention, e.g., the 5H9 or the 1H11 monoclonal antibody disclosed herein. Methods of making and screening monoclonal antibodies are well known in the art.

Once the desired antibody-producing hybridoma has been selected and cloned, the resultant antibody can be produced by any of a number of methods known in the art. For example, the hybridoma can be cultured in vitro in a suitable medium for a suitable length of time, followed by the recovery of the desired antibody from the supernatant. The length of time and medium are known or can be readily determined.

Additionally, recombinant antibodies specific for B7-H5, such as chimeric and humanized monoclonal antibodies comprising both human and non-human portions, are within the scope of the invention. Such chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) *Science* 240, 1041-43; Liu et al. (1987) *J. Immunol.* 139, 3521-26; Sun et al. (1987) *Proc. Natl. Acad. Sci. USA* 84, 214-18; Nishimura et al. (1987) *Canc. Res.* 47, 999-1005; Wood et al. (1985) *Nature* 314, 446-49; Shaw et al. (1988) *J. Natl. Cancer Inst.* 80, 1553-59; Morrison, (1985) *Science* 229, 1202-07; Oi et al. (1986) *BioTechniques* 4, 214; Winter, U.S. Pat. No. 5,225,539; Jones et al. (1986) *Nature* 321, 552-25; Veroeyan et al. (1988) *Science* 239, 1534; and Beidler et al. (1988) *J. Immunol.* 141, 4053-60.

Also included within the scope of the invention are antibody fragments and derivatives which contain at least the functional portion of the antigen binding domain of an antibody that binds specifically to B7-H5. Antibody fragments that contain the binding domain of the molecule can be generated by known techniques. For example, such fragments include, but are not limited to: F(ab')$_2$ fragments which can be produced by pepsin digestion of antibody molecules; Fab fragments which can be generated by reducing the disulfide bridges of F(ab')$_2$ fragments; and Fab fragments which can be generated by treating antibody molecules with papain and a reducing agent. See, e.g., National Institutes of Health, 1 *Current Protocols In Immunology*, Coligan et al., ed. 2.8, 2.10 (Wiley Interscience, 1991). Antibody fragments also include Fv (e.g., single chain Fv (scFv)) fragments, i.e., antibody products in which there are no constant region amino acid residues. Such fragments can be produced, for example, as described in U.S. Pat. No. 4,642,334 which is incorporated herein by reference in its entirety.

Structure of B7-CD28 Family Molecules

All of the B7-like molecules, e.g., B7-H5, and their receptors are type I transmembrane glycoproteins and are members of the immunoglobulin (Ig) superfamily. The members of B7 family share 20-35% identity in their amino acid sequences. Despite such low homology in primary amino acid composition, these molecules share a similar secondary structure: single Ig V-and Ig C-like extracellular domain. Four cysteine residues, which are involved in the formation of the disulfide bonds of the IgV and IgC domains, are well conserved. The receptors for the B7 family are members of the CD28 family, and possess a single IgV-like extracellular domain. Their cytoplasmic tails contain putative SH2- and SH3-motifs thought to be involved in signal transduction.

By crystallography and molecular modeling, tertiary structures for ligands and receptors of the B7-CD28 superfamily have been determined. The interactions of receptor-ligand pairs are mediated predominantly through residues in their IgV domains. In general, IgV domains are described as two-layered β-strands with "front" and "back" sheets. The front and back sheets of CTLA-4 IgV domain consist of strands A'GFCC' and ABEDC", respectively, whereas the front and back sheets of the B7-1/B7-2 IgV domains are composed of strands AGFCC'C" and BED, respectively. The binding faces between CTLA-4/CD28 and B7-1/B7-2 are dominated by the interaction of the CDR3 analogous loop from CTLA-4/CD28, centered on the MYPPPY motif, with the surface formed predominately by conserved residues between B7-1 and B7-2 on the G, F, C, C' and C" strands. The MYPPPY motif is not conserved in inducible costimulatory molecules (ICOS), but a related FDPPPF sequence in the analogous position is identified as a major determinant for binding of ICOS to B7-H2. Although the location of the PD-1 binding sites in B7-H1/B7-DC corresponds to the CTLA-4/CD28 binding sites in B7-1/B7-2, B7-H1 and B7-DC utilize non-conserved residues on their A'GFCC'C" face to bind PD-1. Crystal structures of CTLA-4/B7 complexes contain bivalent homodimers of CTLA-4 with B7-binding sites located distally to the CTLA-4 dimer interface, which suggests that the CTLA-4 homodimer can bind to noncovalent homodimers of B7-1 or B7-2 to form a lattice of CTLA-4/B7 interactions. Formation of such a lattice is thought to trigger the formation of stable signaling complexes as part of the immunological synapse. One of skill in the art will appreciate that the three-dimensional structure of B7-H5 molecules is likely to be similar to that of other B7 family members.

The following example is meant to illustrate, not limit, the invention.

EXAMPLE

A human B7-H5 cDNA (FIG. 1; SEQ ID NO:5) was identified from the NCBI database based on homology to other B7 family molecules, including B7-1 (CD80), B7-2 (CD86), B7-H1 (PD-L1), B7-H2 (B7h/B7RP-1), B7-H3, B7-DC (PD-L2) and B7-H4 (B7x). Full-length human B7-H5 cDNA (FIG. 9; SEQ ID NO:2) was amplified by PCR with PFU polymerase (Stratagene, Calif.) from human placental cDNA (Clontech, Calif.), cloned into pcDNA™ 3.1⁻ vector (Invitrogen, Calif.) and confirmed by DNA sequencing. A mouse B7-H5 cDNA (FIG. 2, SEQ ID NO:6) was identified from the NCBI and Celera databases based on homology to the same B7 family molecules. To isolate the mouse B7-H5 homologue, several sets of primers based on mouse and human EST sequences were used to amplify mouse B7-H5 cDNA (FIG. 10; SEQ ID NO:4) from spleen cDNA of a C57BL/6 (B6) mouse. Full-length mouse B7-H5 cDNA was similarly cloned into pcDNA™ 3.1⁻ vector and confirmed by DNA sequencing.

Molecular models of the N-terminal V-domains of human B7-H5 (FIG. 5) and mouse B7-H5 were built by homology modeling based on the X-ray structures of human CD80 and CD86 (Stamper et al, 2001, *Nature* 410:08-611; Schwartz et al., 2001, *Nature* 410:604-608) using MOE (Molecular Operating Environment, Chemical Computing Group, Quebec, Canada). Insertions and deletions in mouse and human B7-H5 relative to the structural template(s) were modeled employing a protein database segment matching procedure (Levitt, 1992, *J. Mol. Biol.* 226:07-533; Fechteler et al., 1995, *J. Mol. Biol.* 253:114-131) implemented in MOE. Side chain replacements were carried out using a rotamer library (Ponder and Pichards, 1987, *J. Mol. Biol.* 193:775-791) extracted from high-resolution protein data bank structures (Berman et al., 2000, *Nucleic Acids Res.* 28:235-242). Intramolecular contacts and stereochemistry of the models were optimized by limited energy minimization using protein force field parameters (Engh and Huber, 1991, *Acta Crystallogr. A*47: 392-400). Residue mapping studies and computer graphical analysis were carried out with InsightII (MSI, CA). Both human and mouse B7-H5 polypeptides were predicted to contain an IgV-like domain, which is involved in the interaction of B7 molecules with their cognate receptors. The human and mouse B7-H5 polypeptides are also predicted to contain a single transmembrane domain, a cysteine predicted to be involved in dimerization, e.g., heterodimerization, and a tyrosine in the cytoplasmic domain predicted to be phosphorylated during signaling. Two structural cysteines, as indicated in FIG. 3, are highly likely to contribute to the formation of the IgV domain. Additional amino acids can form a non-typical immunoglobulin constant-like region as indicated in FIG. 5.

FIG. 6 shows an alignment of the immunoglobulin superfamily (IgSF) V-domain sequences of the B7 family (h: human, m: mouse), including B7-H5. IgSF V-set consensus residues were defined according to Williams and Barclay (1998, *Annu. Rev. Immunol.* 6:381-405) and Bork et al (1994, *J. Mol. Biol.* 242:309-320), and are shown on a black background. Consensus residue positions are labeled with invariant IgSF residues or conserved residue character (h: hydrophobic, p: polar). Residue positions shown on a gray background are signature residues of the B7 family outside IgSF consensus positions. Beta-strands of the V-domain are designated according to IgSF conventions (A', B, C, C', C", D, F, G). Residue positions labeled with # are involved in dimerization of CD80/CD86 in their crystal structures and residues labeled with asterisks participate in cytotoxic T-lymphocyte-associated protein 4 (CTLA4) binding.

On the basis of this alignment, in both human and mouse B7-H5, 14/16 IgSF V-set consensus residues and 12/13 B7 signature residues are conserved. This is strong evidence that these proteins have V-like B7 domains.

The most unique features in these domains are unusual insertions in the A'-B and C-D loops, including free cysteines. These loops are spatially adjacent in the C-terminal region of the V-domain, at its interface with subsequent regions. The cysteine residues would be available for inter-loop disulfide bonding or, alternatively, covalent interactions with adjacent domains. Given these insertions, the C-terminal region of the B7-H5 V-domain would likely not be capable of forming the interface with a subsequent C-type IgSF domain, as seen in the crystal structure of CD80.

Fusion protein constructs of human B7-H5 polypeptide (FIG. 3; SEQ ID NO:1) and mouse B7-H5 polypeptide (FIG. 4; SEQ ID NO:3) were prepared by cloning the extracellular domain of B7-H5 in frame with the hinge-CH2-CH3 domain of either human IgG1 or mouse IgG2a (Chapoval et al., 2002, *Mol. Biotechnol.* 21:259-264). To enhance the secretion of fusion protein, the native signal peptide of B7-H5 was replaced with the preprotrypsin signal peptide and FLAG sequence derived from pCMV-FLAG™ vector (Sigma, Mo.). To produce the B7-H5Ig fusion proteins, 293T cells were transfected with 10 µg of mouse or human B7-H5Ig constructs by the calcium phosphate method, and B7-H5Igs were purified from culture supernatant by protein G column, as described previously (Dong et al., 1999, *Nature Med.* 5:1365-1369). Stable CHO cell lines expressing human B7-H5 or mock-transfected lines were prepared by cotransfection of pcDNA™ vector containing human B7-H5 cDNA with pLX-SHD, a plasmid encoding histidinol-resistant gene (Miller et al., 1993, *Methods Enzymol.* 217:581-599). Stable clones were selected with 20 mM histidinol (Sigma, Mo.). Clones expressing B7-H5 were screened for binding with human B7-H5 monoclonal antibody (mAb).

Figure 8A:
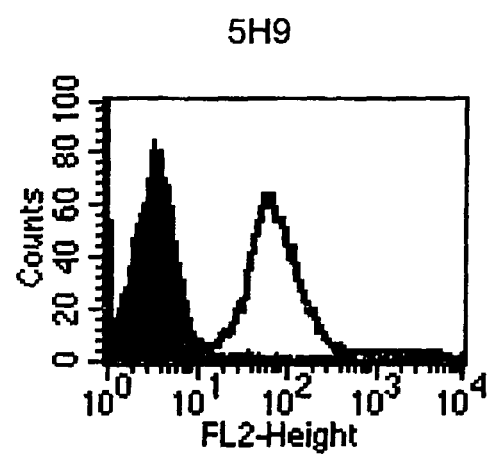
FIG. 8A is a fluorescence flow cytometry (FFC) histogram depicting number of cells (y-axis) with the indicated fluorescence levels (x-axis). CHO cell transfectants expressing human B7-H5 (open) or mock-transfected CHO cells (solid) were stained with the 5H9 monoclonal antibody.
Figure 8B:
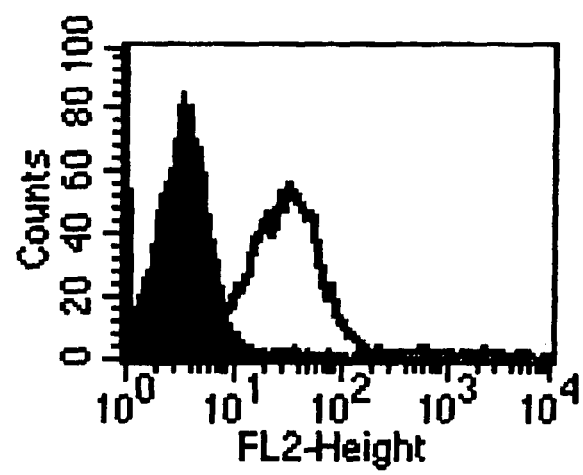
FIG. 8B is a FFC histogram depicting number of cells (y-axis) with the indicated fluorescence levels (x-axis). CHO cell transfectants expressing human B7-H5 (open) or mock-transfected CHO cells (solid) were stained with the 1H11 monoclonal antibody.

Monoclonal antibodies to human B7-H5 were generated by immunization of a BALB/c mouse by immunization methods described previously (Wilcox et al., 2002, *J. Clin. Invest.* 109:651-659). Two hybridomas, 5H9 and 1H11, which secrete mouse IgG1 against human B7-H5 (see FIGS. 8A and 8B) were generated. The monoclonal antibodies produced by the two hybridomas were purified by IgG affinity column chromatography. Specificity of the mAb was determined by negative staining of various transfectants expressing B7 family molecules including B7-1, B7-2, B7-H1, B7-DC, B7-H2 and B7-H3. Control mouse IgG1 were purchased from Rockland (Gilbertville, Pa.).

Figure 7:
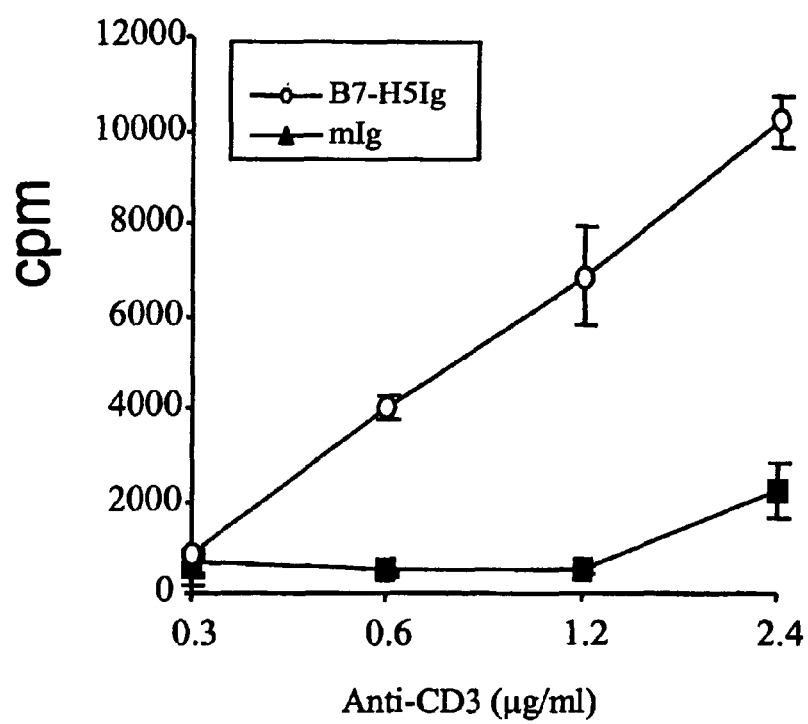
FIG. 7 is a line graph depicting in vitro co-stimulation of T cell proliferation by B7-H5. T cell proliferation is depicted as $^3$H-thymidine incorporation (y-axis; counts per minute, cpm). Anti-CD3 antibody concentration is indicated on the x-axis.

The activity of human B7-H5 to stimulate proliferation of T cells was investigated. Flat bottom 96-well plates were coated with varying concentrations of anti-CD3 mAb (Dong et al, 1999, *Nature Med.* 5:1365-1369), washed extensively, and coated with 10 µg/ml B7-H5Ig or control mIg for 2 hours at 37° C. Nylon wool-purified human CD3+ T cells from peripheral blood mononuclear cells (PBMC) of healthy donors were cultured in the presence of the pre-coated anti-CD3 mAb at 3×10$^5$ cells/well. Seventy-two hours later, the wells were pulsed with 1 µCi of $^3$H-thymidine (TdR) and the proliferation of T cells was determined by incorporation of TdR. The B7-H5Ig fusion protein stimulated T cell proliferation at concentrations as low as 0.6 µg/ml (FIG. 7). This demonstrates that the B7-H5 polypeptide can co-stimulate T cells.

I claim:

1. An isolated polypeptide consisting of an amino acid sequence encoded by a nucleic acid sequence that encodes a protein consisting of an extracellular region of a protein, wherein the nucleic acid sequence hybridizes over its full length, after a wash at 50° C. to 60° C. in a buffer containing 0.2×SSC and 0.1% SDS, to the complement of a nucleotide sequence consisting of nucleotide 88 to nucleotide 936 of SEQ ID NO:2.

2. An isolated polypeptide consisting of all or part of amino acid 30 to amino acid 311 of SEQ ID NO:1 and including at least an V-like Ig domain consisting of amino acid 47 to amino acid 150 of SEQ ID NO:1.

3. The polypeptide of claim 1, wherein the amino acid sequence comprises amino acid 40 to amino acid 190 of SEQ ID NO:1.

4. The isolated polypeptide of claim 1, wherein the amino acid sequence comprises amino acid 35 to amino acid 190 of SEQ ID NO:1.

5. The isolated polypeptide of claim 1, wherein the polypeptide has the ability to co-stimulate a T cell.

6. A fusion protein comprising a first domain and at least one additional domain,
wherein the first domain consists of an amino acid sequence encoded by a nucleic acid sequence that encodes a protein consisting of an extracellular region of a protein, wherein the nucleic acid sequence hybridizes over its full length, after a wash at 50° C. to 60° C. in a buffer containing 0.2×SSC and 0.1% SDS, to the complement of a nucleotide sequence consisting of nucleotide 88 to nucleotide 936 of SEQ ID NO:2 and
the at least one additional domain comprises an amino acid sequence that is unrelated to SEQ ID NO:1.

7. The fusion protein of claim 6, wherein the at least one additional domain is selected from the group consisting of: a heterologous targeting or leader sequence and an amino acid sequence that facilitates purification, detection or solubility of the fusion protein.

8. The fusion protein of claim 6, wherein the at least one additional domain is all or part of an immunoglobulin heavy chain constant region.

9. An isolated antigenic polypeptide consisting of at least 8 consecutive residues of a polypeptide consisting of amino acid 30 to amino acid 311 of SEQ ID NO:1.

10. The polypeptide of claim 1, wherein the nucleic acid sequence hybridizes over its full length, after a wash at 50° C. to 60° C. in a buffer containing 0.2×SSC and 0.1% SDS, to the complement of a nucleotide sequence consisting of nucleotide 88 to nucleotide 570 of SEQ ID NO:2.

11. The polypeptide of claim 1, wherein the amino acid sequence comprises amino acid 30 to amino acid residue 190 of SEQ ID NO:1.

12. The polypeptide of claim 2, wherein the amino acid sequence comprises amino acid 40 to amino acid 311 of SEQ ID NO:1.

13. The polypeptide of claim 2, wherein the amino acid sequence comprises amino acid 35 to amino acid 311 of SEQ ID NO:1.

14. The polypeptide of claim 2, wherein the amino acid sequence comprises amino acid 30 to amino acid 311 of SEQ ID NO:1.

15. A fusion protein comprising a first domain and at least one additional domain, wherein the first domain consists of a polypeptide consisting of all or part of amino acid 30 to amino acid 311 of SEQ ID NO:1 and including at least an V-like Ig domain consisting of amino acid 47 to amino acid 150 of SEQ ID NO:1 and
the at least one additional domain comprises an amino acid sequence that is unrelated to SEQ ID NO:1.

16. The fusion protein of claim 15, wherein the at least one additional domain is selected from the group consisting of: a heterologous targeting or leader sequence and an amino acid sequence that facilitates purification, detection or solubility of the fusion protein.

17. The fusion protein of claim 15, wherein the at least one additional domain is all or part of an immunoglobulin heavy chain constant region.

18. The fusion protein of claim 6, wherein the polypeptide comprises amino acid 40 to amino acid 190 of SEQ ID NO: 1.

19. The fusion protein of claim 6, wherein the polypeptide comprises amino acid 35 to amino acid 190 of SEQ ID NO:1.

20. The fusion protein of claim 6, wherein the polypeptide comprises amino acid 30 to amino acid 190 of SEQ ID NO:1.

21. The fusion protein of claim 15, wherein the polypeptide comprises amino acid 40 to amino acid 311 of SEQ ID NO: 1.

22. The fusion protein of claim 15, wherein the polypeptide comprises amino acid 35 to amino acid 311 of SEQ ID NO:1.

23. The fusion protein of claim 15, wherein the polypeptide comprises amino acid 30 to amino acid 311 of SEQ ID NO:1.

24. An isolated polypeptide consisting of all or part of amino acid 30 to amino acid 309 of SEQ ID NO:3 and including at least a V-like Ig domain consisting of amino acid 47 to amino acid 149 of SEQ ID NO:3.

25. The fusion proteim of claim 6, wherein the nucleic acid sequence hybridizes over its full length, after a wash at 50° C. to 60° C. in a buffer containing 0.2 ×SSC and 0.1% SDS, to the complement of a nucleotide sequence consisting of nucleotide 88 to nucleotide 570 of SEQ ID NO:2.

* * * * *

UNITED STATES PATENT AND TRADEMARK OFFICE
CERTIFICATE OF CORRECTION

| | | |
|---|---|---|
| PATENT NO. | : 7,919,585 B2 | Page 1 of 1 |
| APPLICATION NO. | : 11/571195 | |
| DATED | : April 5, 2011 | |
| INVENTOR(S) | : Lieping Chen | |

It is certified that error appears in the above-identified patent and that said Letters Patent is hereby corrected as shown below:

In Claim 25, delete "proteim" and insert -- protein --, therefor.

Signed and Sealed this
Thirty-first Day of May, 2011

David J. Kappos
*Director of the United States Patent and Trademark Office*

UNITED STATES PATENT AND TRADEMARK OFFICE
CERTIFICATE OF CORRECTION

PATENT NO. : 7,919,585 B2  Page 1 of 1
APPLICATION NO. : 11/571195
DATED : April 5, 2011
INVENTOR(S) : Lieping Chen It is certified that error appears in the above-identified patent and that said Letters Patent is hereby corrected as shown below:

Column 52, line 7 (claim 25, line 1) delete "proteim" and insert -- protein --, therefor.

This certificate supersedes the Certificate of Correction issued May 31, 2011.

Signed and Sealed this
Twenty-eighth Day of June, 2011

David J. Kappos
*Director of the United States Patent and Trademark Office*

SEQUENCE LISTING

```
<160> NUMBER OF SEQ ID NOS: 24

<210> SEQ ID NO 1
<211> LENGTH: 311
<212> TYPE: PRT
<213> ORGANISM: Homo sapiens

<400> SEQUENCE: 1

Met Gly Val Pro Thr Ala Leu Glu Ala Gly Ser Trp Arg Trp Gly Ser
 1               5                  10                  15

Leu Leu Phe Ala Leu Phe Leu Ala Ala Ser Leu Gly Pro Val Ala Ala
                20                  25                  30

Phe Lys Val Ala Thr Pro Tyr Ser Leu Tyr Val Cys Pro Glu Gly Gln
            35                  40                  45

Asn Val Thr Leu Thr Cys Arg Leu Leu Gly Pro Val Asp Lys Gly His
        50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
                100                 105                 110

Leu Ala Gln Arg His Gly Leu Glu Ser Ala Ser Asp His His Gly Asn
            115                 120                 125

Phe Ser Ile Thr Met Arg Asn Leu Thr Leu Leu Asp Ser Gly Leu Tyr
        130                 135                 140

Cys Cys Leu Val Val Glu Ile Arg His His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Glu Ser Glu Asn Ile Thr
            180                 185                 190
```

```
Ala Ala Ala Leu Ala Thr Gly Ala Cys Ile Val Gly Ile Leu Cys Leu
            195                 200                 205

Pro Leu Ile Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Ala Gln Gly Ile Pro Glu
                245                 250                 255

Ala Lys Val Arg His Pro Leu Ser Tyr Val Ala Gln Arg Gln Pro Ser
                260                 265                 270

Glu Ser Gly Arg His Leu Leu Ser Glu Pro Ser Thr Pro Leu Ser Pro
                275                 280                 285

Pro Gly Pro Gly Asp Val Phe Phe Pro Ser Leu Asp Pro Val Pro Asp
                290                 295                 300

Ser Pro Asn Phe Glu Val Ile
305                 310

<210> SEQ ID NO 2
<211> LENGTH: 936
<212> TYPE: DNA
<213> ORGANISM: Homo sapiens
<220> FEATURE:
<221> NAME/KEY: CDS
<222> LOCATION: (1)...(933)

<400> SEQUENCE: 2
```

| | | |
|---|---|---|
| atg ggc gtc ccc acg gcc ctg gag gcc ggc agc tgg cgc tgg gga tcc<br>Met Gly Val Pro Thr Ala Leu Glu Ala Gly Ser Trp Arg Trp Gly Ser<br>1                      5                     10                    15 | | 48 |
| ctg ctc ttc gct ctc ttc ctg gct gcg tcc cta ggt ccg gtg gca gcc<br>Leu Leu Phe Ala Leu Phe Leu Ala Ala Ser Leu Gly Pro Val Ala Ala<br>                    20                     25                    30 | | 96 |
| ttc aag gtc gcc acg ccg tat tcc ctg tat gtc tgt ccc gag ggg cag<br>Phe Lys Val Ala Thr Pro Tyr Ser Leu Tyr Val Cys Pro Glu Gly Gln<br>         35                    40                    45 | | 144 |
| aac gtc acc ctc acc tgc agg ctc ttg ggc cct gtg gac aaa ggg cac<br>Asn Val Thr Leu Thr Cys Arg Leu Leu Gly Pro Val Asp Lys Gly His<br>50                     55                     60 | | 192 |
| gat gtg acc ttc tac aag acg tgg tac cgc agc tcg agg ggc gag gtg<br>Asp Val Thr Phe Tyr Lys Thr Trp Tyr Arg Ser Ser Arg Gly Glu Val<br>65                     70                    75                    80 | | 240 |
| cag acc tgc tca gag cgc cgg ccc atc cgc aac ctc acg ttc cag gac<br>Gln Thr Cys Ser Glu Arg Arg Pro Ile Arg Asn Leu Thr Phe Gln Asp<br>                      85                    90                    95 | | 288 |
| ctt cac ctg cac cat gga ggc cac cag gct gcc aac acc agc cac gac<br>Leu His Leu His His Gly Gly His Gln Ala Ala Asn Thr Ser His Asp<br>                    100                 105               110 | | 336 |
| ctg gct cag cgc cac ggg ctg gag tcg gcc tcc gac cac cat ggc aac<br>Leu Ala Gln Arg His Gly Leu Glu Ser Ala Ser Asp His His Gly Asn<br>           115                    120                 125 | | 384 |
| ttc tcc atc acc atg cgc aac ctg acc ctg ctg gat agc ggc ctc tac<br>Phe Ser Ile Thr Met Arg Asn Leu Thr Leu Leu Asp Ser Gly Leu Tyr<br>         130                    135                 140 | | 432 |
| tgc tgc ctg gtg gtg gag atc agg cac cac cac tcg gag cac agg gtc<br>Cys Cys Leu Val Val Glu Ile Arg His His His Ser Glu His Arg Val<br>145                    150                 155                160 | | 480 |
| cat ggt gcc atg gag ctg cag gtg cag aca ggc aaa gat gca cca tcc<br>His Gly Ala Met Glu Leu Gln Val Gln Thr Gly Lys Asp Ala Pro Ser<br>                             165                 170               175 | | 528 |
| aac tgt gtg gtg tac cca tcc tcc tcc cag gag agt gaa aac atc acg | | 576 |

```
Asn Cys Val Val Tyr Pro Ser Ser Gln Glu Ser Glu Asn Ile Thr
            180                 185                 190 gct gca gcc ctg gct acg ggt gcc tgc atc gta gga atc ctc tgc ctc    624
Ala Ala Ala Leu Ala Thr Gly Ala Cys Ile Val Gly Ile Leu Cys Leu
            195                 200                 205 ccc ctc atc ctg ctc ctg gtc tac aag caa agg cag gca gcc tcc aac    672
Pro Leu Ile Leu Leu Leu Val Tyr Lys Gln Arg Gln Ala Ala Ser Asn
            210                 215                 220 cgc cgt gcc cag gag ctg gtg cgg atg gac agc aac att caa ggg att    720
Arg Arg Ala Gln Glu Leu Val Arg Met Asp Ser Asn Ile Gln Gly Ile
225                 230                 235                 240 gaa aac ccc ggc ttt gaa gcc tca cca cct gcc cag ggg ata ccc gag    768
Glu Asn Pro Gly Phe Glu Ala Ser Pro Pro Ala Gln Gly Ile Pro Glu
                245                 250                 255 gcc aaa gtc agg cac ccc ctg tcc tat gtg gcc cag cgg cag cct tct    816
Ala Lys Val Arg His Pro Leu Ser Tyr Val Ala Gln Arg Gln Pro Ser
                260                 265                 270 gag tct ggg cgg cat ctg ctt tcg gag ccc agc acc ccc ctg tct cct    864
Glu Ser Gly Arg His Leu Leu Ser Glu Pro Ser Thr Pro Leu Ser Pro
            275                 280                 285 cca ggc ccc gga gac gtc ttc ttc cca tcc ctg gac cct gtc cct gac    912
Pro Gly Pro Gly Asp Val Phe Phe Pro Ser Leu Asp Pro Val Pro Asp
            290                 295                 300 tct cca aac ttt gag gtc atc tag                                    936
Ser Pro Asn Phe Glu Val Ile
305                 310

<210> SEQ ID NO 3
<211> LENGTH: 309
<212> TYPE: PRT
<213> ORGANISM: Mus musculus

<400> SEQUENCE: 3

Met Gly Val Pro Ala Val Pro Glu Ala Ser Ser Pro Arg Trp Gly Thr
1               5                   10                  15

Leu Leu Leu Ala Ile Phe Leu Ala Ala Ser Arg Gly Leu Val Ala Ala
            20                  25                  30

Phe Lys Val Thr Thr Pro Tyr Ser Leu Tyr Val Cys Pro Glu Gly Gln
            35                  40                  45

Asn Ala Thr Leu Thr Cys Arg Ile Leu Gly Pro Val Ser Lys Gly His
50                  55                  60

Asp Val Thr Ile Tyr Lys Thr Trp Tyr Leu Ser Ser Arg Gly Glu Val
65                  70                  75                  80

Gln Met Cys Lys Glu His Arg Pro Ile Arg Asn Phe Thr Leu Gln His
            85                  90                  95

Leu Gln His His Gly Ser His Leu Lys Ala Asn Ala Ser His Asp Gln
            100                 105                 110

Pro Gln Lys His Gly Leu Glu Leu Ala Ser Asp His Gly Asn Phe
            115                 120                 125

Ser Ile Thr Leu Arg Asn Val Thr Pro Arg Asp Ser Gly Leu Tyr Cys
            130                 135                 140

Cys Leu Val Ile Glu Leu Lys Asn His His Pro Glu Gln Arg Phe Tyr
145                 150                 155                 160

Gly Ser Met Glu Leu Gln Val Gln Ala Gly Lys Gly Ser Gly Ser Thr
            165                 170                 175

Cys Met Ala Ser Asn Glu Gln Asp Ser Asp Ser Ile Thr Ala Ala Ala
            180                 185                 190

Leu Ala Thr Gly Ala Cys Ile Val Gly Ile Leu Cys Leu Pro Leu Ile
```

-continued

```
                195                 200                 205
Leu Leu Leu Val Tyr Lys Gln Arg Gln Val Ala Ser His Arg Ala
    210                 215                 220

Gln Glu Leu Val Arg Met Asp Ser Ser Asn Thr Gln Gly Ile Glu Asn
225                 230                 235                 240

Pro Gly Phe Glu Thr Thr Pro Pro Phe Gln Gly Met Pro Glu Ala Lys
                245                 250                 255

Thr Arg Pro Pro Leu Ser Tyr Val Ala Gln Arg Gln Pro Ser Glu Ser
            260                 265                 270

Gly Arg Tyr Leu Leu Ser Asp Pro Ser Thr Pro Leu Ser Pro Pro Gly
        275                 280                 285

Pro Gly Asp Val Phe Phe Pro Ser Leu Asp Pro Val Pro Asp Ser Pro
    290                 295                 300

Asn Ser Glu Ala Ile
305

<210> SEQ ID NO 4
<211> LENGTH: 930
<212> TYPE: DNA
<213> ORGANISM: Mus musculus
<220> FEATURE:
<221> NAME/KEY: CDS
<222> LOCATION: (1)...(927)

<400> SEQUENCE: 4 atg ggt gtc ccc gcg gtc cca gag gcc agc agc ccg cgc tgg gga acc      48
Met Gly Val Pro Ala Val Pro Glu Ala Ser Ser Pro Arg Trp Gly Thr
 1               5                  10                  15 ctg ctc ctt gct att ttc ctg gct gca tcc aga ggt ctg gta gca gcc      96
Leu Leu Leu Ala Ile Phe Leu Ala Ala Ser Arg Gly Leu Val Ala Ala
             20                  25                  30 ttc aag gtc acc act cca tat tct ctc tat gtg tgt ccc gag gga cag     144
Phe Lys Val Thr Thr Pro Tyr Ser Leu Tyr Val Cys Pro Glu Gly Gln
         35                  40                  45 aat gcc acc ctc acc tgc agg att ctg ggc ccc gtg tcc aaa ggg cac     192
Asn Ala Thr Leu Thr Cys Arg Ile Leu Gly Pro Val Ser Lys Gly His
     50                  55                  60 gat gtg acc atc tac aag acg tgg tac ctc agc tca cga ggc gag gtc     240
Asp Val Thr Ile Tyr Lys Thr Trp Tyr Leu Ser Ser Arg Gly Glu Val
 65                  70                  75                  80 cag atg tgc aaa gaa cac cgg ccc ata cgc aac ttc aca ttg cag cac     288
Gln Met Cys Lys Glu His Arg Pro Ile Arg Asn Phe Thr Leu Gln His
                 85                  90                  95 ctt cag cac cac gga agc cac ctg aaa gcc aac gcc agc cat gac cag     336
Leu Gln His His Gly Ser His Leu Lys Ala Asn Ala Ser His Asp Gln
            100                 105                 110 ccc cag aag cat ggg cta gag cta gct tct gac cac cac ggt aac ttc     384
Pro Gln Lys His Gly Leu Glu Leu Ala Ser Asp His His Gly Asn Phe
        115                 120                 125 tct atc acc ctg cgc aat gtg acc cca agg gac agc ggc ctc tac tgc     432
Ser Ile Thr Leu Arg Asn Val Thr Pro Arg Asp Ser Gly Leu Tyr Cys
    130                 135                 140 tgt cta gtg ata gaa tta aaa aac cac cac cca gaa caa cgg ttc tac     480
Cys Leu Val Ile Glu Leu Lys Asn His His Pro Glu Gln Arg Phe Tyr
145                 150                 155                 160 ggg tcc atg gag cta cag gta cag gca ggc aaa ggc tcg ggg tcc aca     528
Gly Ser Met Glu Leu Gln Val Gln Ala Gly Lys Gly Ser Gly Ser Thr
                165                 170                 175 tgc atg gcg tct aat gag cag gac agt gac agc atc acg gct gcg gcc     576
Cys Met Ala Ser Asn Glu Gln Asp Ser Asp Ser Ile Thr Ala Ala Ala
```

| | |
|---|---|
| ctg gcc acc ggc gcc tgc atc gtg gga atc ctc tgc ctc ccc ctt atc<br>Leu Ala Thr Gly Ala Cys Ile Val Gly Ile Leu Cys Leu Pro Leu Ile<br>195                       200                     205 | 624 |
| ctg ctg ctg gtc tat aag cag aga cag gtg gcc tct cac cgc cgt gcc<br>Leu Leu Leu Val Tyr Lys Gln Arg Gln Val Ala Ser His Arg Arg Ala<br>210                       215                     220 | 672 |
| cag gag ttg gtg agg atg gac agc agc aac acc caa gga atc gaa aac<br>Gln Glu Leu Val Arg Met Asp Ser Ser Asn Thr Gln Gly Ile Glu Asn<br>225                       230                     235                     240 | 720 |
| cca ggc ttc gag acc act cca ccc ttc cag ggg atg cct gag gcc aag<br>Pro Gly Phe Glu Thr Thr Pro Pro Phe Gln Gly Met Pro Glu Ala Lys<br>                       245                     250                     255 | 768 |
| acc agg ccg cca ctg tcc tat gtg gcc cag cgg caa cct tcg gag tca<br>Thr Arg Pro Pro Leu Ser Tyr Val Ala Gln Arg Gln Pro Ser Glu Ser<br>                     260                     265                     270 | 816 |
| gga cgg tac ctg ctc tct gac ccc agc aca cct ctg tcg cct cca ggc<br>Gly Arg Tyr Leu Leu Ser Asp Pro Ser Thr Pro Leu Ser Pro Pro Gly<br>275                       280                     285 | 864 |
| cct ggg gac gtc ttt ttc cca tcc cta gat cca gtc cct gac tcc cct<br>Pro Gly Asp Val Phe Phe Pro Ser Leu Asp Pro Val Pro Asp Ser Pro<br>290                       295                     300 | 912 |
| aac tct gaa gcc atc taa<br>Asn Ser Glu Ala Ile<br>305 | 930 |

<210> SEQ ID NO 5
<211> LENGTH: 4689
<212> TYPE: DNA
<213> ORGANISM: Homo sapiens
<220> FEATURE:
<221> NAME/KEY: CDS
<222> LOCATION: (60)...(992)

<400> SEQUENCE: 5

| | |
|---|---|
| ccggccgcgt cccgcccgct ccccggcacc agaagttcct ctgcgcgtcc gacggcgac | 59 |
| atg ggc gtc ccc acg gcc ctg gag gcc ggc agc tgg cgc tgg gga tcc<br>Met Gly Val Pro Thr Ala Leu Glu Ala Gly Ser Trp Arg Trp Gly Ser<br>1                     5                     10                     15 | 107 |
| ctg ctc ttc gct ctc ttc ctg gct gcg tcc cta ggt ccg gtg gca gcc<br>Leu Leu Phe Ala Leu Phe Leu Ala Ala Ser Leu Gly Pro Val Ala Ala<br>                     20                     25                     30 | 155 |
| ttc aag gtc gcc acg ccg tat tcc ctg tat gtc tgt ccc gag ggg cag<br>Phe Lys Val Ala Thr Pro Tyr Ser Leu Tyr Val Cys Pro Glu Gly Gln<br>35                       40                     45 | 203 |
| aac gtc acc ctc acc tgc agg ctc ttg ggc cct gtg gac aaa ggg cac<br>Asn Val Thr Leu Thr Cys Arg Leu Leu Gly Pro Val Asp Lys Gly His<br>50                       55                     60 | 251 |
| gat gtg acc ttc tac aag acg tgg tac cgc agc tcg agg ggc gag gtg<br>Asp Val Thr Phe Tyr Lys Thr Trp Tyr Arg Ser Ser Arg Gly Glu Val<br>65                       70                     75                     80 | 299 |
| cag acc tgc tca gag cgc cgg ccc atc cgc aac ctc acg ttc cag gac<br>Gln Thr Cys Ser Glu Arg Arg Pro Ile Arg Asn Leu Thr Phe Gln Asp<br>                     85                     90                     95 | 347 |
| ctt cac ctg cac cat gga ggc cac cag gct gcc aac acc agc cac gac<br>Leu His Leu His His Gly Gly His Gln Ala Ala Asn Thr Ser His Asp<br>                     100                   105                   110 | 395 |
| ctg gct cag cgc cac ggg ctg gag tcg gcc tcc gac cac cat ggc aac<br>Leu Ala Gln Arg His Gly Leu Glu Ser Ala Ser Asp His His Gly Asn<br>115                       120                     125 | 443 |
| ttc tcc atc acc atg cgc aac ctg acc ctg ctg gat agc ggc ctc tac | 491 |

```
Phe Ser Ile Thr Met Arg Asn Leu Thr Leu Leu Asp Ser Gly Leu Tyr
        130                 135                 140 tgc tgc ctg gtg gtg gag atc agg cac cac cac tcg gag cac agg gtc       539
Cys Cys Leu Val Val Glu Ile Arg His His His Ser Glu His Arg Val
145                 150                 155                 160 cat ggt gcc atg gag ctg cag gtg cag aca ggc aaa gat gca cca tcc       587
His Gly Ala Met Glu Leu Gln Val Gln Thr Gly Lys Asp Ala Pro Ser
                165                 170                 175 aac tgt gtg gtg tac cca tcc tcc tcc cag gag agt gaa aac atc acg       635
Asn Cys Val Val Tyr Pro Ser Ser Ser Gln Glu Ser Glu Asn Ile Thr
            180                 185                 190 gct gca gcc ctg gct acg ggt gcc tgc atc gta gga atc ctc tgc ctc       683
Ala Ala Ala Leu Ala Thr Gly Ala Cys Ile Val Gly Ile Leu Cys Leu
        195                 200                 205 ccc ctc atc ctg ctc ctg gtc tac aag caa agg cag gca gcc tcc aac       731
Pro Leu Ile Leu Leu Leu Val Tyr Lys Gln Arg Gln Ala Ala Ser Asn
    210                 215                 220 cgc cgt gcc cag gag ctg gtg cgg atg gac agc aac att caa ggg att       779
Arg Arg Ala Gln Glu Leu Val Arg Met Asp Ser Asn Ile Gln Gly Ile
225                 230                 235                 240 gaa aac ccc ggc ttt gaa gcc tca cca cct gcc cag ggg ata ccc gag       827
Glu Asn Pro Gly Phe Glu Ala Ser Pro Pro Ala Gln Gly Ile Pro Glu
                245                 250                 255 gcc aaa gtc agg cac ccc ctg tcc tat gtg gcc cag cgg cag cct tct       875
Ala Lys Val Arg His Pro Leu Ser Tyr Val Ala Gln Arg Gln Pro Ser
            260                 265                 270 gag tct ggg cgg cat ctg ctt tcg gag ccc agc acc ccc ctg tct cct       923
Glu Ser Gly Arg His Leu Leu Ser Glu Pro Ser Thr Pro Leu Ser Pro
        275                 280                 285 cca ggc ccc gga gac gtc ttc ttc cca tcc ctg gac cct gtc cct gac       971
Pro Gly Pro Gly Asp Val Phe Phe Pro Ser Leu Asp Pro Val Pro Asp
    290                 295                 300 tct cca aac ttt gag gtc atc tagcccagct gggggacagt gggctgttgt        1022
Ser Pro Asn Phe Glu Val Ile
305             310 ggctgggtct gggcaggtg catttgagcc agggctggct ctgtgagtgg cctccttggc     1082
ctcggccctg gttccctccc tcctgctctg ggctcagata ctgtgacatc ccagaagccc    1142
agcccctcaa cccctctgga tgctacatgg ggatgctgga cggctcagcc cctgttccaa    1202
ggattttggg gtgctgagat tctcccctag agacctgaaa ttcaccagct acagatgcca    1262
aatgacttac atcttaagaa gtctcagaac gtccagccct tcagcagctc tcgttctgag    1322
acatgagcct tgggatgtgg cagcatcagt gggacaagat ggacactggg ccaccctccc    1382
aggcaccaga cacagggcac ggtggagaga cttctcccccc gtggccgcct tggctccccc   1442
gttttgcccg aggctgctct tctgtcagac ttcctctttg taccacagtg gctctggggc    1502
caggcctgcc tgcccactgg ccatcgccac cttacccagc tgcctcctac cagcagtttc    1562
tctgaagatc tgtcaacagg ttaagtcaat ctggggcttc cactgcctgc attccagtcc    1622
ccagagcttg gtggtcccga acgggaagt acatattggg gcatggtggc ctccgtgagc     1682
aaatggtgtc ttgggcaatc tgaggccagg acagatgttg cccacccac tggagatggt     1742 gctgagggag gtgggtgggg ccttctggga aggtgagtgg agaggggcac ctgcccccccg    1802 ccctcccat cccctactcc cactgctcag cgcgggccat tgcaagggtg ccacacaatg     1862
tcttgtccac cctgggacac ttctgagtat gaagcgggat gctattaaaa actacatggg   1922
gaaacaggtg caaccctgg agatggattg taagagccag tttaaatctg cactctgctg    1982
ctcctccccc accccaccct tccactccat acaatctggg cctggtggag tcttcgcttc    2042
```

```
agagccattc ggccaggtgc gggtgatgtt cccatctcct gcttgtgggc atgccctggc    2102
tttgttttta tacacatagg caaggtgagt cctctgtgga attgtgattg aaggatttta    2162
aagcagggga ggagagtagg gggcatctct gtacactctg ggggtaaaac agggaaggca    2222
gtgcctgagc atggggacag gtgaggtggg gctgggcaga ccccctgtag cgtttagcag    2282
gatgggggcc ccaggtactg tggagagcat agtccagcct gggcatttgt ctcctagcag    2342
cctacactgg ctctgctgag ctgggcctgg gtgctgaaag ccaggatttg ggctaggcg     2402 ggaagatgtt cgcccaattg cttgggggt tgggggatg gaaaagggga gcacctctag      2462
gctgcctggc agcagtgagc cctgggcctg tggctacagc cagggaaccc cacctggaca    2522
catggccctg cttctaagcc ccccagttag gcccaaagga atggtccact gagggcctcc    2582
tgctctgcct gggctgggcc aggggctttg aggagagggt aaacataggc ccggagatgg    2642
ggctgacacc tcgagtggcc agaatatgcc caaaccccgg cttctcccctt gtccctaggc   2702 agagggggt cccttctttt gttccctctg gtcaccacaa tgcttgatgc cagctgccat     2762
aggaagaggg tgctggctgg ccatggtggc acacacctgt cctcccagca ctttgcaggg    2822
ctgaggtgga aggaccgctt aagcccaggt gttcaaggct gctgtgagct gtgttcgagc    2882
cactacactc cagcctgggg acggagcaaa actttgcctc aaaacaaatt ttaaaaagaa    2942 agaagaagg aaagagggta tgtttttcac aattcatggg ggcctgcatg gcaggagtgg     3002
ggacaggaca cctgctgttc ctggagtcga aggacaagcc cacagcccag attccggttc    3062
tcccaactca ggaagagcat gccctgccct ctggggaggc tggcctggcc ccagccctca    3122
gctgctgacc ttgaggcaga acaacttct aagaatttgg ctgccagacc ccaggcctgg     3182
ctgctgctgt gtggagaggg aggcggcccg cggcagaaca gccaccgcac ttcctcctca    3242
gcttcctctg gtgcggccct gccctctctt ctctggaccc ttttacaact gaacgcatct    3302
gggcttcgtg gtttcctgtt ttcagcgaaa tttactctga gctcccagtt ccatcttcat    3362
ccatggccac aggccctgcc tacaacgcac tagggacgtc cctccctgct gctgctgggg    3422
aggggcaggc tgctggagcc gccctctgag ttgcccggga tggtagtgcc tctgatgcca    3482
gccctggtgg ctgtgggctg gggtgcatgg agagctggg tgcgagaaca tggcgcctcc     3542 aggggcggg aggagcacta ggggctgggg caggaggctc ctggagcgct ggattcgtgg     3602
cacagtctga ggccctgaga gggaaatcca tgcttttaag aactaattca ttgttaggag    3662
atcaatcagg aattaggggc catcttacct atctcctgac attcacagtt taatagagac    3722
ttcctgcctt tattccctcc cagggagagg ctgaaggaat ggaattgaaa gcaccatttg    3782
gagggttttg ctgacacagc ggggaccgct cagcactccc taaaaacaca ccatggaggc    3842
cactggtgac tgctggtggg caggctggcc ctgcctgggg gagtccgtgg cgatgggcgc    3902
tggggtggag gtgcaggagc ccaggacct gcttttcaaa agacttctgc ctgaccagag     3962
ctcccactac atgcagtggc cagggcaga ggggctgata catggccttt ttcagggggt     4022
gctcctcgcg gggtggactt ggagtgtgc agtgggacag ggggctgcag ggtcctgcc      4082 accaccgagc accaacttgg cccctggggt cctgccccat gaatgaggcc ttccccaggg    4142
ctggcctgac tgtgctgggg gctgggttaa cgttttctca gggaaccaca atgcacgaaa    4202
gaggaactgg ggttgctaac caggatgctg ggaacaaagg cctcttgaag cccagccaca    4262
gcccagctga gcatgaggcc cagcccatag acggcacagg ccacctggcc cattccctgg    4322
gcattccctg ctttgcattg ctgcttctct tcaccccatg gaggctatgt caccctaact    4382
atcctggaat gtgttgagag ggattctgaa tgatcaatat agcttggtga gacagtgccg    4442
```

-continued

```
agatagatag ccatgtctgc cttgggcacg ggagagggaa gtggcagcat gcatgctgtt    4502
tcttggcctt ttctgttaga atacttggtg ctttccaaca cactttcaca tgtgttgtaa    4562
cttgtttgat ccaccccctt ccctgaaaat cctgggaggt tttattgctg ccatttaaca    4622
cagagggcaa tagaggttct gaaaggtctg tgtcttgtca aaacaagtaa acggtggaac    4682
tacgact                                                              4689
```

```
<210> SEQ ID NO 6
<211> LENGTH: 4795
<212> TYPE: DNA
<213> ORGANISM: Mus musculus
<220> FEATURE:
<221> NAME/KEY: CDS
<222> LOCATION: (120)...(1046)

<400> SEQUENCE: 6
```

```
gagcattcac tctagcgagc gagcggcgtg tacagccggc tccctgggct cctggagtcc     60
cgcttgctcc aagcgcactc cagcagtctc tttctgctct tgcccggctc gacggcgac    119 atg ggt gtc ccc gcg gtc cca gag gcc agc agc ccg cgc tgg gga acc     167
Met Gly Val Pro Ala Val Pro Glu Ala Ser Ser Pro Arg Trp Gly Thr
 1               5                  10                  15 ctg ctc ctt gct att ttc ctg gct gca tcc aga ggt ctg gta gca gcc     215
Leu Leu Leu Ala Ile Phe Leu Ala Ala Ser Arg Gly Leu Val Ala Ala
             20                  25                  30 ttc aag gtc acc act cca tat tct ctc tat gtg tgt ccc gag gga cag     263
Phe Lys Val Thr Thr Pro Tyr Ser Leu Tyr Val Cys Pro Glu Gly Gln
         35                  40                  45 aat gcc acc ctc acc tgc agg att ctg ggc ccc gtg tcc aaa ggg cac     311
Asn Ala Thr Leu Thr Cys Arg Ile Leu Gly Pro Val Ser Lys Gly His
     50                  55                  60 gat gtg acc atc tac aag acg tgg tac ctc agc tca cga ggc gag gtc     359
Asp Val Thr Ile Tyr Lys Thr Trp Tyr Leu Ser Ser Arg Gly Glu Val
 65                  70                  75                  80 cag atg tgc aaa gaa cac cgg ccc ata cgc aac ttc aca ttg cag cac     407
Gln Met Cys Lys Glu His Arg Pro Ile Arg Asn Phe Thr Leu Gln His
                 85                  90                  95 ctt cag cac cac gga agc cac ctg aaa gcc aac gcc agc cat gac cag     455
Leu Gln His His Gly Ser His Leu Lys Ala Asn Ala Ser His Asp Gln
            100                 105                 110 ccc cag aag cat ggg cta gag cta gct tct gac cac cac ggt aac ttc     503
Pro Gln Lys His Gly Leu Glu Leu Ala Ser Asp His His Gly Asn Phe
        115                 120                 125 tct atc acc ctg cgc aat gtg acc cca agg gac agc ggc ctc tac tgc     551
Ser Ile Thr Leu Arg Asn Val Thr Pro Arg Asp Ser Gly Leu Tyr Cys
    130                 135                 140 tgt cta gtg ata gaa tta aaa aac cac cac cca gaa caa cgg ttc tac     599
Cys Leu Val Ile Glu Leu Lys Asn His His Pro Glu Gln Arg Phe Tyr
145                 150                 155                 160 ggg tcc atg gag cta cag gta cag gca ggc aaa ggc tcg ggg tcc aca     647
Gly Ser Met Glu Leu Gln Val Gln Ala Gly Lys Gly Ser Gly Ser Thr
                165                 170                 175 tgc atg gcg tct aat gag cag gac agt gac agc atc acg gct gcg gcc     695
Cys Met Ala Ser Asn Glu Gln Asp Ser Asp Ser Ile Thr Ala Ala Ala
            180                 185                 190 ctg gcc acc ggc gcc tgc atc gtg gga atc ctc tgc ctc ccc ctt atc     743
Leu Ala Thr Gly Ala Cys Ile Val Gly Ile Leu Cys Leu Pro Leu Ile
        195                 200                 205 ctg ctg ctg gtc tat aag cag aga cag gtg gcc tct cac cgc cgt gcc     791
Leu Leu Leu Val Tyr Lys Gln Arg Gln Val Ala Ser His Arg Arg Ala
```

```
            210                 215                 220
cag gag ttg gtg agg atg gac agc agc aac acc caa gga atc gaa aac    839
Gln Glu Leu Val Arg Met Asp Ser Ser Asn Thr Gln Gly Ile Glu Asn
225                 230                 235                 240 cca ggc ttc gag acc act cca ccc ttc cag ggg atg cct gag gcc aag    887
Pro Gly Phe Glu Thr Thr Pro Pro Phe Gln Gly Met Pro Glu Ala Lys
                245                 250                 255 acc agg ccg cca ctg tcc tat gtg gcc cag cgg caa cct tcg gag tca    935
Thr Arg Pro Pro Leu Ser Tyr Val Ala Gln Arg Gln Pro Ser Glu Ser
            260                 265                 270 gga cgg tac ctg ctc tct gac ccc agc aca cct ctg tcg cct cca ggc    983
Gly Arg Tyr Leu Leu Ser Asp Pro Ser Thr Pro Leu Ser Pro Pro Gly
        275                 280                 285 cct ggg gac gtc ttt ttc cca tcc cta gat cca gtc cct gac tcc cct   1031
Pro Gly Asp Val Phe Phe Pro Ser Leu Asp Pro Val Pro Asp Ser Pro
    290                 295                 300 aac tct gaa gcc atc taaaccagct ggggaaccat gaaccatggt acctgggtca   1086
Asn Ser Glu Ala Ile
305 gggatatgtg cacttgatct atggctggcc cttggacagt cttttaggca ctgactccag   1146 cttccttgct cctgctctga gcctagactc tgcttttaca agatgcacag accctcccct   1206 atctctttca gacgctactt gggggcagg gagaagatgt tggattgctc attgctgttc     1266 tcaagatctt gggatgctga gttctcccta gagacttgac ttcgacagcc acagatgtca   1326 gatgacctgc atcctatgaa cgtccggctt ggcaagagcc tttcttcatg gaaaccagta   1386 gcccggaggg gatgaggtag gcaccttgcc accctcccgg gagagagaca caagatgtga   1446 gagactcctg ctcactgtgg gggtgtggct ggcctgcttg tttgcctgag gatgctcctc   1506 tgttggactg actctatccc cctggattct ggagcttggc tggcctatgt cccaccagag   1566 gagcatctca gcagccttcc accagcaacc tgagggcctg ccagcttcgt ggctctgggc   1626 tctcattacc tgtatggccg tccacagagc tcagtggcca gaggctttga acaggaagt   1686 acatgtcagg ttcaggaacc actgtgagct cattagtgtc ttgagcaatg tgaggcctgg   1746 accagtggac acggagggag ggtggcgaga ggatgatggg gatgatgagg ggaacacgct   1806 cccttcctgt ccttgtcatc caccactacc actattcagt gtggagcagt ggcaaaggtg   1866 accgacctcc acaatgtcct agtgatgctg gaccatttct aagtgtgaaa gagatgctat   1926 taaaaacagt atgtggcaat ggctgccaac agctgagtgg actggaggca ctggctttaa   1986 ggccctggag gtgcagggcc cggtatgggg atagggatgg gagtttcagt gagggcctag   2046 ggatcactcc gcttctgacc actcttcttc tgagcctcac ctcagggtga ccttcaggca   2106 cacagaaagag cttgccctg gtccgatact actcttggct ctcatctcca gggtttggca   2166 tgacctgggc acacaggggg agtcttcaga aaggatttta aagcatgaaa agaaagggta   2226 gttcttgtga ggtagggatg ggcagctgat gtttgagagt gaggagggat acggctgggc   2286 agatcactct ccagtctcta gagggaaagt agctctaagt ctgggagagc agcagcccag   2346 tggtaccata tgtcttcttg cagcttccac tggctgggct gaactgggca tgggtaggaa   2406 agctcctgtt ctgggcctgc agccagggag aaccccattc attccctgag acagatggg   2466 tggggagaga agagagagtt tcaggccggg aagcagcaat aagctatctg ctggggaccc   2526 agacaagttg tctgatgagg tccaagatgt gggatgccag ttatacctgg ggcttgggga   2586 tccttagagg ctttgtatca tcatcatagg agtgtcgggg tggccagggc atcaaagcca   2646 tgaccccctgt tttatcctca gggtccactc ttctgcacca tccattgctc tagatctatg   2706
```

```
cagttactat agacagaatg tgttgttctg tttggctttg gggataatgg cctggcgaac   2766
tgccagctgt tcagtggcag ggctgtgagg ccagtcaaag actagaaccc acagaccagc   2826
tgaacgatga gtatagcctg tccctgggg gagcctgacc tgtctccagc cctaagcttc    2886
agacctcacc actcagatga cttctaagaa tttgcctgtg ggaccctg catggctgca     2946 gctccgtgga aaggagagga ggccccagc agaagaacca ctcgcttcct gcccagcttc    3006
ctcctgtagg gctctaagtc tcttcttctt gggaccctgc aagcaaaggc atgtcagctt   3066
ggtggtttcc tgttttgggt gaagttttgt gtggtccggg ttctgtctac atccatgaac   3126
ttggggtgct accaccttgc tgctgctgta gagacagctg caggatctta gggtggaaaa   3186
tggaggtgcc ctgaggtgct agcccttggg gcaaagatg gggtggcaat gagacacagt    3246
ggggaactga gttccccaag aggagggagg agccctgtag cctcaaggc catattgggt     3306 tcctggtacc agcaaaagcc tagagagcga agtctgtatt ttgaggaggt aattgatcct   3366
tacggaatcc atcagaaatt tggagcgggt gctttatcta tctctggagg gtctctacct   3426
atctccgatg aagctctccc tgggcctggg atgggagaaa ccaggaggaa aggtgtctga   3486
taaagcaggg gcttcttgac aagccaaagg gccactggta gctgttgtgg accgagctga   3546
ccctgctgaa gtattgtagt gtgccttgga ccaacttctc aaaagagcaa ccccggggct   3606
accctacttc tgccaggaag aggcggagaa ggggctgaga ggcctggaag gggctagctc   3666
cttctttgag aactgctccc cggaggactt ggaggaggcg gctaggctac gggctgctga   3726
gggccctttg tctttcctaa cctgggcact gttaggatgc tccctcctgg aaaaggcttt   3786
cctgggtgtg agctagagca gtgtccatgc cagcgctgaa cctgccatgg tgggagctga   3846
actaaaaatt tctcagggaa ctaaaatagg caaaagagga actggggag gagggtgcca    3906 ggcaggatgg ggggaaggga gggcagtgca aaagtctctt gaaacacaga cagcccagct   3966
gagtgccagt cccagatcac agagaatacg gctcatctgg ctcatgttct gcatgcttgc   4026
tgctttaccc tggcactttc cttctccacc atgagtgcga gtcctgggag tcctgggagg   4086
gtgaggatta atgccagcct ggggagcaga tagctgacag agtccttggg taactggctt   4146
gaaccaggac ctcaggattc cactctgggg atctagcttt gtctgggcca gtgaagatct   4206
ctataatggc attattgcca ggggataaac atttcactgg gttctgatct gttgggtgtg   4266
gcttcctgga aaatatggtg agaggaattc tgctaaggat acagttgata agaaagttct   4326
gagattgatt agtaatgcct gccttggact caggaaggga agtggcagta tgaatgccat   4386
gtcttaatca ttttggttaa aatatgcttc ccaaaagatt tccacgtgtg ttcttgttta   4446
tttgacatct gtctccatat cagtcttgaa agcctttctg tgtgtatata tatgatgttt   4506
gcgtgtatat atgttttgt gtgtgcatat ggaagtcaga aatcactggg tgtcttcctc    4566
cattcctttg caatgtatgt tttttttttt tttacgattt atttactata tgaatgtttt   4626
gcctgaatac atgcataggt gtcacgtaca tgcctgctgg aacgcttgga actggagtta   4686
caggtggcta tgagctacag tgtgagcact gggaatcaaa cctgggtctt ctgcaagagc   4746
aacaaattaa aagtcagctc ttaactactt gagctatttt tccaactcc               4795
```

<210> SEQ ID NO 7
<211> LENGTH: 25
<212> TYPE: PRT
<213> ORGANISM: Homo sapiens

<400> SEQUENCE: 7

```
Met Ala Ile Ser Gly Val Pro Val Leu Gly Phe Phe Ile Ile Ala Val
 1               5                  10                  15
```

```
Leu Met Ser Ala Gln Glu Ser Trp Ala
            20              25
```

<210> SEQ ID NO 8
<211> LENGTH: 5
<212> TYPE: PRT
<213> ORGANISM: Homo sapiens

<400> SEQUENCE: 8

```
Lys Phe Glu Arg Gln
 1               5
```

<210> SEQ ID NO 9
<211> LENGTH: 15
<212> TYPE: PRT
<213> ORGANISM: Homo sapiens

<400> SEQUENCE: 9

```
Met Asp Asp Gln Arg Asp Leu Ile Ser Asn Asn Glu Gln Leu Pro
 1               5                  10                  15
```

<210> SEQ ID NO 10
<211> LENGTH: 4
<212> TYPE: PRT
<213> ORGANISM: Homo sapiens

<400> SEQUENCE: 10

```
Lys Asp Glu Leu
 1
```

<210> SEQ ID NO 11
<211> LENGTH: 105
<212> TYPE: PRT
<213> ORGANISM: Homo sapiens

<400> SEQUENCE: 11

```
Ile His Val Thr Lys Glu Val Lys Glu Val Ala Thr Leu Ser Cys Gly
 1               5                  10                  15

His Asn Val Ser Val Glu Glu Leu Ala Gln Thr Arg Ile Tyr Trp Gln
            20                  25                  30

Lys Glu Lys Lys Met Val Leu Thr Met Met Ser Gly Asp Met Asn Ile
        35                  40                  45

Trp Pro Glu Tyr Lys Asn Arg Thr Ile Phe Asp Ile Thr Asn Asn Leu
    50                  55                  60

Ser Ile Val Ile Leu Ala Leu Arg Pro Ser Asp Glu Gly Thr Tyr Glu
65                  70                  75                  80

Cys Val Val Leu Lys Tyr Glu Lys Asp Ala Phe Lys Arg Glu His Leu
                85                  90                  95

Ala Glu Val Thr Leu Ser Val Lys Ala
            100                 105
```

<210> SEQ ID NO 12
<211> LENGTH: 109
<212> TYPE: PRT
<213> ORGANISM: Homo sapiens

<400> SEQUENCE: 12

```
Leu Lys Ile Gln Ala Tyr Phe Asn Glu Thr Ala Asp Leu Pro Cys Gln
 1               5                  10                  15

Phe Ala Asn Ser Gln Asn Gln Ser Leu Ser Glu Leu Val Val Phe Trp
            20                  25                  30
```

```
Gln Asp Gln Glu Asn Leu Val Leu Asn Glu Val Tyr Leu Gly Lys Glu
            35                  40                  45

Lys Phe Asp Ser Val His Ser Lys Tyr Met Gly Arg Thr Ser Phe Asp
     50                  55                  60

Ser Asp Ser Trp Thr Leu Arg Leu His Asn Leu Gln Ile Lys Asp Lys
 65                  70                  75                  80

Gly Leu Tyr Gln Cys Ile Ile His His Lys Lys Pro Thr Gly Met Ile
                 85                  90                  95

Arg Ile His Gln Met Asn Ser Glu Leu Ser Val Leu Ala
                100                 105
```

<210> SEQ ID NO 13
<211> LENGTH: 113
<212> TYPE: PRT
<213> ORGANISM: Homo sapiens

<400> SEQUENCE: 13

```
Asp Leu Tyr Val Val Glu Tyr Gly Ser Asn Met Thr Ile Glu Cys Lys
 1               5                  10                  15

Phe Pro Val Glu Lys Gln Leu Asp Leu Ala Ala Leu Ile Val Tyr Trp
                20                  25                  30

Glu Met Glu Asp Lys Asn Ile Ile Gln Phe Val His Gly Glu Glu Asp
            35                  40                  45

Leu Lys Val Gln His Ser Ser Tyr Arg Gln Arg Ala Arg Leu Leu Lys
     50                  55                  60

Asp Gln Leu Ser Leu Gly Asn Ala Ala Leu Gln Ile Thr Asp Val Lys
 65                  70                  75                  80

Leu Gln Asp Ala Gly Val Tyr Arg Cys Met Ile Ser Tyr Gly Gly Ala
                 85                  90                  95

Asp Tyr Lys Arg Ile Thr Val Lys Val Asn Ala Pro Tyr Asn Lys Ile
                100                 105                 110

Asn
```

<210> SEQ ID NO 14
<211> LENGTH: 113
<212> TYPE: PRT
<213> ORGANISM: Mus musculus

<400> SEQUENCE: 14

```
Asp Leu Tyr Val Val Glu Tyr Gly Ser Asn Val Thr Met Glu Cys Arg
 1               5                  10                  15

Phe Pro Val Glu Arg Glu Leu Asp Leu Leu Ala Leu Val Val Tyr Trp
                20                  25                  30

Glu Lys Glu Asp Glu Gln Val Ile Gln Phe Val Ala Gly Glu Glu Asp
            35                  40                  45

Leu Lys Pro Gln His Ser Asn Phe Arg Gly Arg Ala Ser Leu Pro Lys
     50                  55                  60

Asp Gln Leu Leu Lys Gly Asn Ala Ala Leu Gln Ile Thr Asp Val Lys
 65                  70                  75                  80

Leu Gln Asp Ala Gly Val Tyr Cys Cys Ile Ile Ser Tyr Gly Gly Ala
                 85                  90                  95

Asp Tyr Lys Arg Ile Thr Leu Lys Val Asn Ala Pro Tyr Arg Lys Ile
                100                 105                 110

Asn
```

<210> SEQ ID NO 15
<211> LENGTH: 114

```
<212> TYPE: PRT
<213> ORGANISM: Homo sapiens

<400> SEQUENCE: 15

Lys Glu Val Arg Ala Met Val Gly Ser Asp Val Glu Leu Ser Cys Ala
 1               5                  10                  15

Cys Pro Glu Gly Ser Arg Phe Asp Leu Asn Asp Val Tyr Val Tyr Trp
            20                  25                  30

Gln Thr Ser Glu Ser Lys Thr Val Val Thr Tyr His Ile Pro Gln Asn
        35                  40                  45

Ser Ser Leu Glu Asn Val Asp Ser Arg Tyr Arg Asn Arg Ala Leu Met
    50                  55                  60

Ser Pro Ala Gly Leu Met Arg Gly Asp Phe Ser Leu Arg Leu Phe Asn
65                  70                  75                  80

Val Thr Pro Gln Asp Glu Gln Lys Phe His Cys Leu Val Leu Ser Gln
                85                  90                  95

Ser Leu Gly Phe Gln Glu Val Ser Val Glu Val Thr Leu His Val
            100                 105                 110

Ala Ala

<210> SEQ ID NO 16
<211> LENGTH: 110
<212> TYPE: PRT
<213> ORGANISM: Homo sapiens

<400> SEQUENCE: 16

Asp Pro Val Val Ala Leu Val Gly Thr Asp Ala Thr Leu Cys Cys Ser
 1               5                  10                  15

Pro Ser Pro Glu Pro Gly Phe Ser Leu Ala Gln Leu Asn Leu Ile Trp
            20                  25                  30

Gln Leu Thr Asp Thr Gln Leu Val His Ser Phe Ala Glu Gly Gln Asp
        35                  40                  45

Gln Gly Ser Ala Tyr Ala Asn Arg Thr Ala Leu Phe Pro Asp Leu Leu
    50                  55                  60

Ala Gln Gly Asn Ala Ser Leu Arg Leu Gln Arg Val Arg Val Ala Asp
65                  70                  75                  80

Glu Gly Ser Phe Thr Cys Phe Val Ser Ile Arg Asp Phe Gly Ser Ala
                85                  90                  95

Ala Val Ser Leu Gln Val Ala Ala Pro Tyr Ser Lys Pro Ser
            100                 105                 110

<210> SEQ ID NO 17
<211> LENGTH: 98
<212> TYPE: PRT
<213> ORGANISM: Homo sapiens

<400> SEQUENCE: 17

Glu Leu Tyr Ile Ile Glu His Gly Ser Asn Val Thr Leu Glu Cys Asn
 1               5                  10                  15

Phe Asp Thr Gly Ser His Val Asn Leu Gly Ala Ile Thr Ala Ser Leu
            20                  25                  30

Gln Lys Val Glu Asn Asp Thr Ser Pro His Arg Glu Arg Ala Thr Leu
        35                  40                  45

Leu Glu Glu Gln Leu Pro Leu Gly Lys Ala Ser Phe His Leu Pro Gln
    50                  55                  60

Val Gln Val Arg Asp Glu Gly Gln Tyr Gln Cys Ile Ile Ile Tyr Gly
65                  70                  75                  80
```

```
Val Ala Trp Asp Tyr Lys Tyr Leu Thr Leu Lys Val Lys Ala Ser Tyr
            85                  90                  95

Arg Lys

<210> SEQ ID NO 18
<211> LENGTH: 98
<212> TYPE: PRT
<213> ORGANISM: Mus musculus

<400> SEQUENCE: 18

Glu Val Tyr Thr Val Asp Val Gly Ser Ser Val Ser Leu Glu Cys Asp
1               5                   10                  15

Phe Asp Arg Arg Glu Cys Thr Glu Leu Glu Gly Ile Arg Ala Ser Leu
            20                  25                  30

Gln Lys Val Glu Asn Asp Thr Ser Leu Gln Ser Glu Arg Ala Thr Leu
        35                  40                  45

Leu Glu Glu Gln Leu Pro Leu Gly Lys Ala Leu Phe His Ile Pro Ser
    50                  55                  60

Val Gln Val Arg Asp Ser Gly Gln Tyr Arg Cys Leu Val Ile Cys Gly
65                  70                  75                  80

Ala Ala Trp Asp Tyr Lys Tyr Leu Thr Val Lys Val Lys Ala Ser Tyr
                85                  90                  95

Met Arg

<210> SEQ ID NO 19
<211> LENGTH: 118
<212> TYPE: PRT
<213> ORGANISM: Homo sapiens

<400> SEQUENCE: 19

Ile Thr Val Thr Thr Val Ala Ser Ala Gly Asn Ile Gly Glu Asp Gly
1               5                   10                  15

Ile Leu Ser Cys Thr Phe Glu Pro Asp Ile Lys Leu Ser Asp Ile Val
            20                  25                  30

Ile Gln Trp Leu Lys Glu Gly Val Leu Gly Leu Val His Glu Phe Lys
        35                  40                  45

Glu Gly Lys Asp Glu Leu Ser Glu Gln Asp Glu Met Phe Arg Gly Arg
    50                  55                  60

Thr Ala Val Phe Ala Asp Gln Val Ile Val Gly Asn Ala Ser Leu Arg
65                  70                  75                  80

Leu Lys Asn Val Gln Leu Thr Asp Ala Gly Thr Tyr Lys Cys Tyr Ile
                85                  90                  95

Ile Thr Ser Lys Gly Lys Gly Asn Ala Asn Leu Glu Tyr Lys Thr Gly
            100                 105                 110

Ala Phe Ser Met Pro Glu
        115

<210> SEQ ID NO 20
<211> LENGTH: 118
<212> TYPE: PRT
<213> ORGANISM: Mus musculus

<400> SEQUENCE: 20

Ile Thr Val Thr Thr Phe Thr Ser Ala Gly Asn Ile Gly Glu Asp Gly
1               5                   10                  15

Thr Leu Ser Cys Thr Phe Glu Pro Asp Ile Lys Leu Asn Gly Ile Val
            20                  25                  30

Ile Gln Trp Leu Lys Glu Gly Ile Lys Gly Leu Val His Glu Phe Lys
```

```
                35                  40                  45
Glu Gly Lys Asp Asp Leu Ser Gln Gln His Glu Met Phe Arg Gly Arg
 50                  55                  60

Thr Ala Val Phe Ala Asp Gln Val Val Gly Asn Ala Ser Leu Arg
 65                  70                  75                  80

Leu Lys Asn Val Gln Leu Thr Asp Ala Gly Thr Tyr Thr Cys Tyr Ile
                 85                  90                  95

Arg Thr Ser Lys Gly Lys Gly Asn Ala Asn Leu Glu Tyr Lys Thr Gly
                100                 105                 110

Ala Phe Ser Met Pro Glu
            115

<210> SEQ ID NO 21
<211> LENGTH: 138
<212> TYPE: PRT
<213> ORGANISM: Homo sapiens

<400> SEQUENCE: 21

Phe Lys Val Ala Thr Pro Tyr Ser Leu Tyr Val Cys Pro Glu Gly Gln
 1               5                  10                  15

Asn Val Thr Leu Thr Cys Arg Leu Leu Gly Pro Val Asp Lys Gly His
                 20                  25                  30

Asp Val Thr Phe Tyr Lys Thr Trp Tyr Arg Ser Ser Arg Gly Glu Val
                 35                  40                  45

Gln Thr Cys Ser Glu Arg Arg Pro Ile Arg Asn Leu Thr Phe Gln Asp
 50                  55                  60

Leu His Leu His His Gly Gly His Gln Ala Ala Asn Thr Ser His Asp
 65                  70                  75                  80

Leu Ala Gln Arg His Gly Leu Glu Ser Ala Ser Asp His His Gly Asn
                 85                  90                  95

Phe Ser Ile Thr Met Arg Asn Leu Thr Leu Leu Asp Ser Gly Leu Tyr
                100                 105                 110

Cys Cys Leu Val Val Glu Ile Arg His His Ser Glu His Arg Val
            115                 120                 125

His Gly Ala Met Glu Leu Gln Val Gln Thr
            130                 135

<210> SEQ ID NO 22
<211> LENGTH: 137
<212> TYPE: PRT
<213> ORGANISM: Mus musculus

<400> SEQUENCE: 22

Phe Lys Val Thr Thr Pro Tyr Ser Leu Tyr Val Cys Pro Glu Gly Gln
 1               5                  10                  15

Asn Ala Thr Leu Thr Cys Arg Ile Leu Gly Pro Val Ser Lys Gly His
                 20                  25                  30

Asp Val Thr Ile Tyr Lys Thr Trp Tyr Leu Ser Ser Arg Gly Glu Val
                 35                  40                  45

Gln Met Cys Lys Glu His Arg Pro Ile Arg Asn Phe Thr Leu Gln His
 50                  55                  60

Leu Gln His His Gly Ser His Leu Lys Ala Asn Ala Ser His Asp Gln
 65                  70                  75                  80

Pro Gln Lys His Gly Leu Glu Leu Ala Ser Asp His His Gly Asn Phe
                 85                  90                  95

Ser Ile Thr Leu Arg Asn Val Thr Pro Arg Asp Ser Gly Leu Tyr Cys
                100                 105                 110
```

```
Cys Leu Val Ile Glu Leu Lys Asn His His Pro Glu Gln Arg Phe Tyr
        115                 120                 125

Gly Ser Met Glu Leu Gln Val Gln Ala
        130                 135

<210> SEQ ID NO 23
<211> LENGTH: 6
<212> TYPE: PRT
<213> ORGANISM: Artificial Sequence
<220> FEATURE:
<223> OTHER INFORMATION: exemplary motif

<400> SEQUENCE: 23

Met Tyr Pro Pro Pro Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: exemplary motif

<400> SEQUENCE: 24

Phe Asp Pro Pro Pro Phe
1               5
```